United States Patent
Kawakami

(10) Patent No.: US 8,276,539 B2
(45) Date of Patent: Oct. 2, 2012

(54) NANOMATERIAL OBSERVATION SAMPLE PREPARATION APPARATUS AND PREPARATION METHOD

(75) Inventor: Tomonori Kawakami, Hamamatsu (JP)

(73) Assignee: Hamamatsu-Photonics K.K., Hamamatsu-shi, Shizuoka (JP)

( * ) Notice: Subject to any disclaimer, the term of this patent is extended or adjusted under 35 U.S.C. 154(b) by 654 days.

(21) Appl. No.: 12/365,256

(22) Filed: Feb. 4, 2009

(65) Prior Publication Data
US 2009/0194418 A1 Aug. 6, 2009

(30) Foreign Application Priority Data
Feb. 6, 2008 (JP) ................. P2008-026847

(51) Int. Cl.
*B05B 5/025* (2006.01)
*B05C 11/00* (2006.01)
*C12N 15/88* (2006.01)

(52) U.S. Cl. ........ 118/638; 118/629; 118/663; 118/671; 118/712; 239/690; 239/706; 435/285.2

(58) Field of Classification Search .......... 118/620–643, 118/663, 667, 712, 713, 671; 427/483, 421, 427/479, 475, 485; 423/285.2, 285.3, 458, 423/459, 470, 471; 239/690, 695, 696, 706; 435/285.2, 285.3, 458, 459, 470, 471, 287.1, 435/287.3

See application file for complete search history.

(56) References Cited

U.S. PATENT DOCUMENTS
6,060,128 A * 5/2000 Kim et al. .................... 427/483
2007/0157880 A1 7/2007 Tanioka et al.

FOREIGN PATENT DOCUMENTS
| JP | S62-238439 | 10/1987 |
| JP | H5-290779 | 11/1993 |
| JP | 2001-281252 | 10/2001 |
| JP | 2002-511792 | 4/2002 |
| JP | 2005-125181 | 5/2005 |
| JP | 2007-52009 | 3/2007 |
| JP | 2007-229851 | 9/2007 |
| WO | WO 2004/074172 | 9/2004 |

OTHER PUBLICATIONS

Osamu, Yogi, et al., "Droplet Formation Technique Using Electrostatic Force and its Application," Journal of the Japan Society of Applied Electromagnetics and Mechanics, vol. 11, No. 3, Sep. 10, 2003, pp. 154-160.

* cited by examiner

*Primary Examiner* — Yewebdar Tadesse
(74) *Attorney, Agent, or Firm* — Drinker Biddle & Reath LLP

(57) ABSTRACT

An observation sample is prepared by immobilizing a nanomaterial on a substrate 10 by applying a voltage between a nanomaterial dispersion liquid 13, filled in an interior of an electrostatic spray nozzle 20, and the observation substrate 10 to electrostatically spray and dry the dispersion liquid 13 and electrostatically deposit the nanomaterial. With respect to the observation substrate 10, including a conductive grid portion 11 and a supporting film 12, a reference electrode 81 is disposed below the substrate 10 and a bias voltage of the same polarity as the electrostatic spraying voltage is applied to the grid portion 11 of the substrate 10 to adjust immobilization positions of the nanomaterial on the substrate 10. An observation sample, with which the nanomaterial is immobilized in a satisfactory state on the substrate, can thereby be prepared.

5 Claims, 12 Drawing Sheets

(a)

(b)

(a)

(b)

(a)

(b)

(a)

(b)

(a)

(b)

(a)

(b)

(a)

(b)

NANOMATERIAL OBSERVATION SAMPLE PREPARATION APPARATUS AND PREPARATION METHOD

BACKGROUND OF THE INVENTION

1. Field of the Invention

Figure 1:
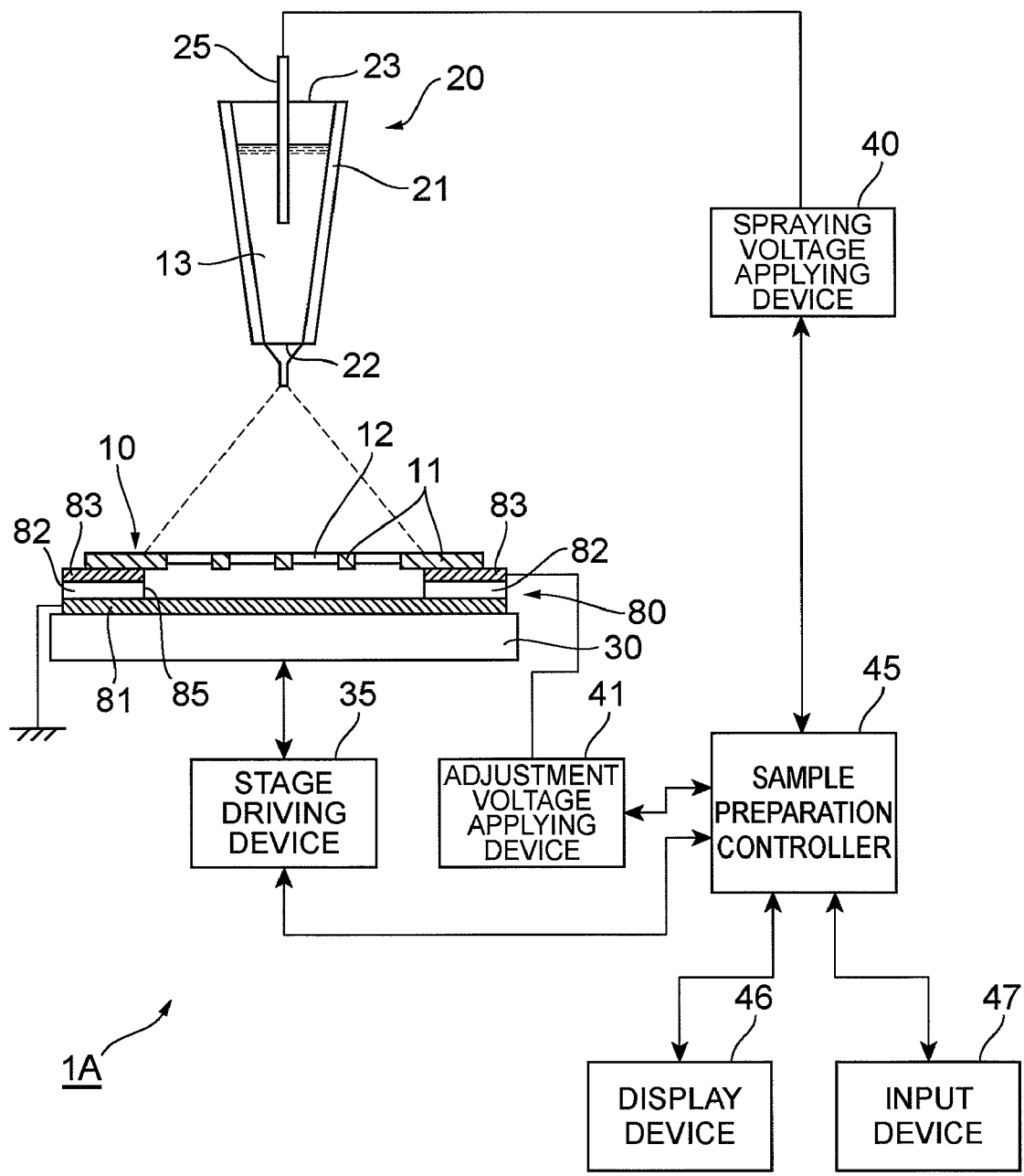

The present invention relates to an observation sample preparation apparatus and an observation sample preparation method for preparing an observation sample for observing a nanomaterial by immobilizing the nanomaterial on an observation substrate by electrostatically spraying a dispersion liquid in which the nanomaterial is dispersed in a solvent.

2. Related Background of the Invention

With recent advances in nanotechnology, a wide variety of nanomaterials have been created. Because new characteristics not seen in normal, bulk body materials are expressed in nanomaterials due to effects of their ultramicroscopic size, etc., nanomaterials are anticipated for utilization in various fields and applications.

Unlike bulk materials, the above-described nanomaterials are difficult to handle due to being extremely small and have a property that a plurality of nanomaterials aggregate readily to form aggregates. Thus, in many cases, nanomaterials are handled in a state of a nanomaterial dispersion liquid, in which a nanomaterial is dispersed in a solvent. As an example of a method for using such a nanomaterial, there is a method for immobilizing the nanomaterial on a substrate of a bulk material (see, for example, Patent Document 1).

Patent Document 1: International Publication No.

SUMMARY OF THE INVENTION

As a means of directly observing a nanomaterial, a Scanning Electron Microscope (SEM) or a Transmission Electron Microscope (TEM) is used. Especially, under circumstances where nanomaterials are gradually becoming smaller in size, there is an increasing need to observe nanomaterials by TEM, which enables observations to be made at high resolution. Generally, in TEM observation of a nanomaterial, an observation substrate, including a conductive grid portion having a mesh-like form and a nanomaterial supporting thin film disposed at the opening of the grid portion, is employed, and a method for preparing an observation sample for TEM observation by immobilizing the nanomaterial on the supporting film of the observation substrate is employed.

Here, as a method for immobilizing the nanomaterial to be observed on the supporting film of the observation substrate, there is a method for coating a nanomaterial dispersion liquid, in which the nanomaterial is dispersed, onto the substrate surface. However, with this method, there is a problem that the nanomaterial aggregates in a process of drying a solvent after coating of the nanomaterial dispersion liquid. When the nanomaterial forms an aggregate, a shape, size, etc., of each individual particle of the nanomaterial cannot be observed.

As another method for immobilizing a nanomaterial on the observation substrate, an electrostatic spray method for spraying a nanomaterial dispersion liquid onto the substrate may be considered (Patent Document 1). With the electrostatic spray method, a high voltage is applied to a capillary-like nozzle filled with the nanomaterial dispersion liquid and charged droplets of the dispersion liquid are sprayed toward the substrate from a dispersion liquid spray outlet at a nozzle tip to immobilize the nanomaterial on a substrate surface. However, examination of preparation of a TEM observation sample using the electrostatic spray method by the present inventor has shown that the charged nanomaterial sprayed from the nozzle deposits more readily on the conductive grid portion than on the supporting film of the observation substrate. In this case, the nanomaterial is not immobilized adequately on the supporting film used for TEM observation and an observation sample of satisfactory state cannot be obtained.

The present invention has been made to solve the above problem, and an object thereof is to provide an observation sample preparation apparatus and an observation sample preparation method enabling an observation sample, used for observation of a nanomaterial and with which the nanomaterial is immobilized on a substrate, to be prepared in a satisfactory state.

To achieve the above object, an observation sample preparation apparatus according to the present invention is a preparation apparatus, preparing an observation sample by immobilizing a nanomaterial on an observation substrate, and includes: (1) an electrostatic spray nozzle, including a nozzle body, having a tubular structure capable of storing, in an interior thereof, a nanomaterial dispersion liquid, in which a nanomaterial is dispersed in a solvent, and having a dispersion liquid spray outlet, provided at a tip of the tubular structure, for electrostatically spraying the nanomaterial dispersion liquid; (2) a substrate support, supporting an observation substrate, which includes a conductive grid portion having a mesh-like form with one or a plurality of openings and a nanomaterial supporting film disposed at the opening of the grid portion and on which the nanomaterial to be observed is immobilized, so that the observation substrate opposes the dispersion liquid spray outlet of the electrostatic spray nozzle; (3) a reference electrode, disposed at an opposite side of the observation substrate from the electrostatic spray nozzle and so as to be spaced apart from the observation substrate and electrically connected to a reference potential; (4) a spraying voltage applying unit, applying an electrostatic spraying voltage between the nanomaterial dispersion liquid and the reference electrode; and (5) an adjustment voltage applying unit, applying a bias voltage, of the same polarity as the electrostatic spraying voltage and used for adjusting a position of immobilization of the nanomaterial on the observation substrate, between the grid portion of the observation substrate and the reference electrode.

An observation sample preparation method according to the present invention is a preparation method for preparing an observation sample by immobilizing a nanomaterial on an observation substrate and includes: (a) a dispersion liquid introducing step of using an electrostatic spray nozzle, including a nozzle body, having a tubular structure capable of storing, in an interior thereof, a nanomaterial dispersion liquid, in which a nanomaterial is dispersed in a solvent, and having a dispersion liquid spray outlet, provided at a tip of the tubular structure, for electrostatically spraying the nanomaterial dispersion liquid, and introducing the nanomaterial dispersion liquid into the interior of the nozzle body; (b) a substrate setting step of setting an observation substrate, including a conductive grid portion having a mesh-like form with one or a plurality of openings and a nanomaterial supporting film disposed at the opening of the grid portion and on which the nanomaterial to be observed is immobilized, so that the observation substrate opposes the dispersion liquid spray outlet of the electrostatic spray nozzle; (c) a spraying voltage applying step of applying, with respect to a reference electrode, disposed at an opposite side of the observation substrate from the electrostatic spray nozzle and so as to be spaced apart from the observation substrate and electrically connected to a reference potential, an electrostatic spraying voltage between the nanomaterial dispersion liquid and the reference electrode; (d) an adjustment voltage applying step of applying a bias voltage, of the same polarity as the electrostatic spraying voltage and used for adjusting a position of immobilization of the nanomaterial on the observation substrate, between the grid portion of the observation substrate and the reference electrode; and (e) a sample preparation step of immobilizing the nanomaterial on the observation substrate to prepare an observation sample by electrostatically spraying the nanomaterial dispersion liquid onto the observation substrate from the dispersion liquid spray outlet of the electrostatic spray nozzle and electrostatically depositing the nanomaterial on a surface of the observation substrate.

With the above-described observation sample preparation apparatus and preparation method, the nanomaterial observation sample is prepared by immobilizing the nanomaterial on the observation substrate by applying a predetermined voltage between the nanomaterial dispersion liquid, filled in the interior of the electrostatic spray nozzle, and the substrate to electrostatically spray and dry the dispersion liquid and electrostatically deposit the nanomaterial. With such a configuration, aggregation of the nanomaterial particles on the observation substrate can be suppressed in comparison to a method for coating the nanomaterial dispersion liquid onto the substrate surface, etc.

Furthermore, in regard to the observation substrate including the conductive grid portion and the supporting film, in the nanomaterial immobilization, the observation substrate is not directly set to the reference potential (for example, a ground potential) but the reference electrode (for example, a ground electrode) is provided separately at the opposite side of the substrate from the nozzle. A trajectory of the nanomaterial from the nozzle toward the substrate and the immobilization position on the substrate are adjusted by applying the bias voltage of the same polarity as the electrostatic spraying voltage to the grid portion of the observation substrate. Deposition of the nanomaterial on the grid portion is thereby suppressed to enable the nanomaterial to be immobilized adequately on the supporting film between the grids and an observation sample of satisfactory state to be prepared.

Such an observation sample can be used favorably, for example, as an observation sample for TEM observation of the nanomaterial such as described above. As the nanomaterial to be subject to observation, a material with a size not more than 100 nm (for example, nanoparticles with a diameter not more than 100 nm) is preferably used.

With the above-described observation sample preparation apparatus and preparation method, the observation sample is prepared by immobilizing the nanomaterial on the observation substrate by applying the voltage between the nanomaterial dispersion liquid, filled in the interior of the nozzle, and the substrate to electrostatically spray the dispersion liquid and electrostatically deposit the nanomaterial, the reference electrode is disposed at the opposite side of the observation substrate, including the conductive grid portion and the supporting film, from the nozzle, and the bias voltage of the same polarity as the electrostatic spraying voltage is applied to the grid portion to adjust the nanomaterial immobilization position to thereby suppress deposition of the nanomaterial on the grid portion and enable a nanomaterial observation sample of satisfactory state to be prepared.

The present invention will be more fully understood from the detailed description given hereinbelow and the accompanying drawings, which are given by way of illustration only and are not to be considered as limiting the present invention.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will be apparent to those skilled in the art from this detailed description.

BRIEF DESCRIPTION OF THE DRAWINGS

FIG. 1 is a block diagram of a configuration of a first embodiment of an observation sample preparation apparatus.

FIG. 2 is a plan view of an example of a configuration of an observation substrate.

FIG. 3 is a schematic view of an embodiment of an observation sample preparation method.

FIG. 4 shows diagrams concerning nanomaterial immobilization positions on the observation substrate.

FIG. 5 shows diagrams of a specific example of a configuration of a voltage application jig.

FIG. 6 shows diagrams of a configuration for housing a nozzle and a substrate stage in a spray chamber.

FIG. 7 shows enlarged views of a configuration of a tip of a modification example of an electrostatic spray nozzle.

FIG. 8 shows views of a configuration of a tip of another modification example of an electrostatic spray nozzle.

FIG. 9 shows views of a configuration of a tip of another modification example of an electrostatic spray nozzle.

FIG. 10 shows diagrams of a specific example of a configuration of an electrostatic spray nozzle.

FIG. 11 shows diagrams of a modification example of a configuration of an electrostatic spray nozzle.

FIG. 12 is a block diagram of a configuration of a second embodiment of an observation sample preparation apparatus.

DESCRIPTION OF THE PREFERRED EMBODIMENTS

Preferred embodiments of a nanomaterial observation sample preparation apparatus and an observation sample preparation method according to the present invention shall now be described in detail along with the drawings. In the description of the drawings, elements that are the same are provided with the same symbol and redundant description shall be omitted. Dimensional proportions in the drawings do not necessarily match those of the description.

FIG. 1 is a schematic block diagram of a configuration of a first embodiment of an observation sample preparation apparatus according to the present invention. The observation sample preparation apparatus 1A according to the present embodiment prepares an observation sample of a nanomaterial by immobilizing the nanomaterial on a surface of an observation substrate by using a nanomaterial dispersion liquid, in which the nanomaterial is dispersed in a solvent, and electrostatically spraying the dispersion liquid. As the nanomaterial subject to the immobilization process and sample preparation, a microscopic material with a size not more than 100 nm (for example, nanoparticles with a diameter not more than 100 nm) is preferably used. Such a microscopic material exhibits physical properties (optical characteristics, electrical characteristics, physical characteristics, etc.) that differ from those of normal, bulk material.

As shown by an example of a configuration of the observation substrate 10 in a plan view of FIG. 2, the observation substrate 10, including a conductive grid portion 11 having a mesh-like form with one or a plurality of openings, and nanomaterial supporting films 12 disposed at openings of the grid portion 11 and on which the nanomaterial to be observed is immobilized, is used as the observation substrate on which the nanomaterial is immobilized.

Figure 2:
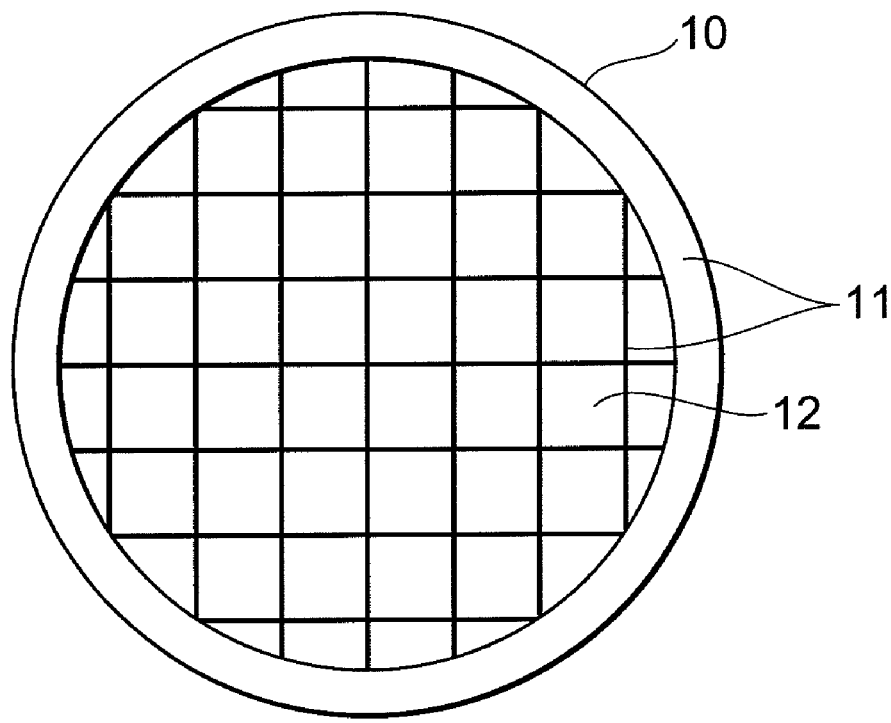

With the example shown in FIG. 2, a plurality of openings are formed in a two-dimensional matrix form in the mesh structure of the circular grid portion 11, and a supporting film 12 is formed in each opening. Such an observation substrate 10 can be used favorably, for example, as an observation substrate for TEM observation. In this configuration, for example, a grid made of copper or other metal may be used for the grid portion 11. As the nanomaterial supporting films 12, for example, thin films of resin, may be used.

The observation sample preparation apparatus 1A shown in FIG. 1 includes an electrostatic spray nozzle 20, a substrate stage 30, on which the observation substrate 10 is set, a spraying voltage applying device 40, an adjustment voltage applying device 41, and a sample preparation controller 45. In this configuration, a vertical direction in the figure that is directed from the nozzle 20 to the substrate 10 on the stage 30 is a nanomaterial spraying axis in the preparation apparatus 1A. In FIG. 1, the observation substrate 10 is disposed in a horizontal direction and the spraying axis extends in a perpendicular direction with respect to a surface of the substrate 10.

The electrostatic spray nozzle 20 is for electrostatically spraying the nanomaterial dispersion liquid 13, in which the nanomaterial is dispersed in the solvent, and has a nozzle body 21, having a tubular structure capable of storing the nanomaterial dispersion liquid 13 in its interior. In the present embodiment, the nozzle 20 is installed with a longitudinal axis of the tubular structure of the nozzle body 21 (central axis of the nozzle) being matched to the nanomaterial spraying axis. Of openings 22 and 23 at respective ends of the nozzle body 21, one of the openings, that is, the opening 22 disposed at the lower end in FIG. 1 is configured as a dispersion liquid spray outlet for electrostatically spraying the dispersion liquid 13 onto the substrate 10. The nozzle 20 having the nozzle body 21 can be prepared using a glass capillary made of a glass material.

With respect to the electrostatic spray nozzle 20 filled with the nanomaterial dispersion liquid 13, the observation substrate 10, which is the target of nanomaterial immobilization, is set on the substrate stage 30, positioned below the nozzle 20, so as to oppose the dispersion liquid spray outlet 22 of the nozzle 20. The substrate stage 30 is a substrate support that supports the observation substrate 10 in a predetermined state with respect to the electrostatic spray nozzle 20.

In a case where adjustment of a setting position of the substrate 10, etc., needs to be performed, an XY stage, movable in X and Y directions (horizontal directions), or an XYZ stage, movable in the X and Y directions (horizontal directions) and a Z direction (vertical direction), may be used as the substrate stage 30. In this case, a stage driving device 35 for driving and controlling the stage is provided for the substrate stage 30 as shown in FIG. 1. If adjustment of the position of the sample 10 is unnecessary or adjustment of the position of the sample 10 is to be performed by adjustment of a position of the nozzle 20, a fixed stage may be used as the substrate stage 30. In this case, the stage driving device 35 is unnecessary.

With the preparation apparatus 1A according to the present embodiment, a jig 80 is interposed between the observation substrate 10 and the substrate stage 30. That is, the observation substrate 10 is supported by the jig 80 being set on the substrate stage 30 and the substrate 10 being disposed on the jig 80. The jig 80 has a reference electrode 81, an insulating layer 82, and a bias electrode 83 laminated in that order from the substrate stage 30 side toward the substrate 10 side and is configured as a voltage application jig used for applying a bias voltage to the grid portion 11 of the observation substrate 10.

The reference electrode 81 forms a substrate stage 30 side portion of the voltage application jig 80 and is disposed at the opposite side of the observation substrate 10 from the electrostatic spray nozzle 20 and so as to be spaced apart (electrically separated) by a predetermined distance from the substrate 10. The reference electrode 81 is electrically connected to a predetermined reference potential. In the example of FIG. 1, the reference potential is a ground potential, and the reference electrode 81 is thus configured as a ground electrode.

The bias electrode 83 forms an observation substrate 10 side (nozzle 20 side) portion of the voltage application jig 80 and supports the substrate 10 by contacting an annular frame portion that forms an outer peripheral portion of the grid portion 11 (see FIG. 2). The bias electrode 83 is thereby connected electrically to the grid portion 11 of the substrate 10. The insulating layer 82 is disposed between the reference electrode 81 and the bias electrode 83, and the jig 80 is configured with the reference electrode 81, the insulating layer 82, and the bias electrode 83 being made integral. The bias electrode 83 is disposed so as to be spaced apart (electrically separated) from the reference electrode 81 by the insulating layer 82.

With this configuration, the reference electrode 81 is formed to oppose an entirety of the substrate 10, including positions opposing the nanomaterial supporting films 12 of the observation substrate 10. Meanwhile, the insulating layer 82 and the bias electrode 83 are configured to support the substrate 10 at the frame portion of the grid portion 11 as mentioned above, and a region opposing the supporting films 12 at an inner side of the annular frame portion is configured as an opening 85 at which the insulating layer 82 and the bias electrode 83 are removed. The jig 80 is thus configured to enable the reference electrode 81 to be in view from the supporting film 12 of the observation substrate 10.

With respect to the reference electrode 81 disposed below the observation substrate 10 and connected to the ground potential, an electrode 25 is disposed at the opening 23 side of an upper end of the nozzle body 21 in the interior of the nozzle body 21 of the electrostatic spray nozzle 20 in a state of being electrically connected to the dispersion liquid 13. The spraying voltage applying device 40 is connected to the electrode 25. By a predetermined voltage being applied from the spraying voltage applying device 40 to the nanomaterial dispersion liquid 13 via the electrode 25, an electrostatic spraying voltage is applied between the dispersion liquid 13 inside the nozzle 20 and the reference electrode 81 at the ground potential.

The adjustment voltage applying device 41 is connected to the bias electrode 83, spaced apart from the reference electrode 81 and electrically connected to the grid portion 11 of the observation substrate 10. By a predetermined voltage being applied to the grid portion 11 of the substrate 10 from the adjustment voltage applying device 41 and via the electrode 83, the bias voltage is applied between the grid portion 11 of the substrate 10 and the reference electrode 81 at the ground potential. The bias voltage is the same in polarity as the electrostatic spraying voltage and is used for adjustment of nanomaterial immobilization positions on the substrate 10.

The sample preparation controller 45 is provided for the preparation apparatus 1A, including the nozzle 20, the substrate stage 30, the voltage application jig 80, and the voltage applying devices 40 and 41. The controller 45 controls operations of respective portions of the preparation apparatus 1A to control conditions of nanomaterial observation sample preparation using the substrate 10 and control execution of the sample preparation. In particular, the controller 45 has a function of a voltage controller that controls the electrostatic spraying voltage applied to the dispersion liquid 13 by the spraying voltage applying device 40 and the bias voltage applied to the grid portion 11 of the substrate 10 by the adjustment voltage applying device 41 according to specific sample preparation conditions. In regard to voltage application by the voltage applying devices 40 and 41, a configuration where manual control by an operator is performed is also possible.

With the configuration shown in FIG. 1, a display device 46 and an input device 47 are connected to the sample preparation controller 45. The display device 46 is used to display necessary information concerning sample preparation process setting conditions, processing circumstances, processing results, etc., to the operator. The input device 47 is used to input necessary information concerning the sample preparation process.

The observation sample preparation method according to the present invention that is executed using the preparation apparatus 1A shown in FIG. 1 shall now be described. In the preparation method, first, the nanomaterial dispersion liquid, in which the nanomaterial to be subject to observation sample preparation is dispersed in the solvent, is prepared and, for the electrostatic spray nozzle 20, the dispersion liquid 13 is introduced into the interior of the nozzle body 21 (dispersion liquid introducing step). As shall be described later, the introduction of the dispersion liquid 13 is performed from the opening 23 at the upper end of the nozzle body 21 or from the dispersion liquid spray outlet 22, which is the lower end opening, according to a specific configuration, etc., of the preparation apparatus 1A.

The observation substrate 10, which, with respect to the nanomaterial dispersion liquid 13, is the substrate for observation sample preparation, is prepared. As the observation substrate 10, a substrate, including the grid portion 11 and the nanomaterial supporting film 12 as described above, is used. The substrate 10 is set on the voltage application jig 80, and the jig 80 and the substrate 10 are set on the substrate stage 30 so as to oppose the spray outlet 22 of the nozzle 20 (substrate setting step). Here, in regard to setting the substrate 10, the substrate 10 may be set in advance before introduction of the dispersion liquid 13 into the nozzle 20.

Next, the spraying voltage applying device 40 and the adjustment voltage applying device 41 are driven and controlled by the controller 45 to apply the voltages necessary for nanomaterial sample preparation. That is, the spraying voltage applying device 40 is driven and controlled to apply the electrostatic spraying voltage to the nanomaterial dispersion liquid 13 inside the nozzle 20 with respect to the reference electrode 81 at the ground potential disposed below the substrate 10 (spraying voltage applying step). Also, the adjustment voltage applying device 41 is driven and controlled to apply the bias voltage to the grid portion 11 of the substrate 10 via the bias electrode 83 with respect to the reference electrode 81 at the ground potential (adjustment voltage applying step). The bias voltage for immobilization position adjustment is of the same polarity as the electrostatic spraying voltage as mentioned above and is set to a predetermined voltage smaller in absolute value than the electrostatic spraying voltage.

In this state where the voltages are being applied, the dispersion liquid 13 is electrostatically sprayed onto the observation substrate 10 from the spray outlet 22 of the nozzle 20, and with each individual droplet of the nanomaterial dispersion liquid 13 sprayed from the nozzle 20, the solvent contained in the droplet is dried in a spray atmosphere. Then, by electrostatically depositing the nanomaterial contained in the dispersion liquid 13 onto the surface of the substrate 10 in a solvent-dried state, the nanomaterial is immobilized on the substrate 10 to thereby prepare the observation sample (sample preparation step).

Figure 3:
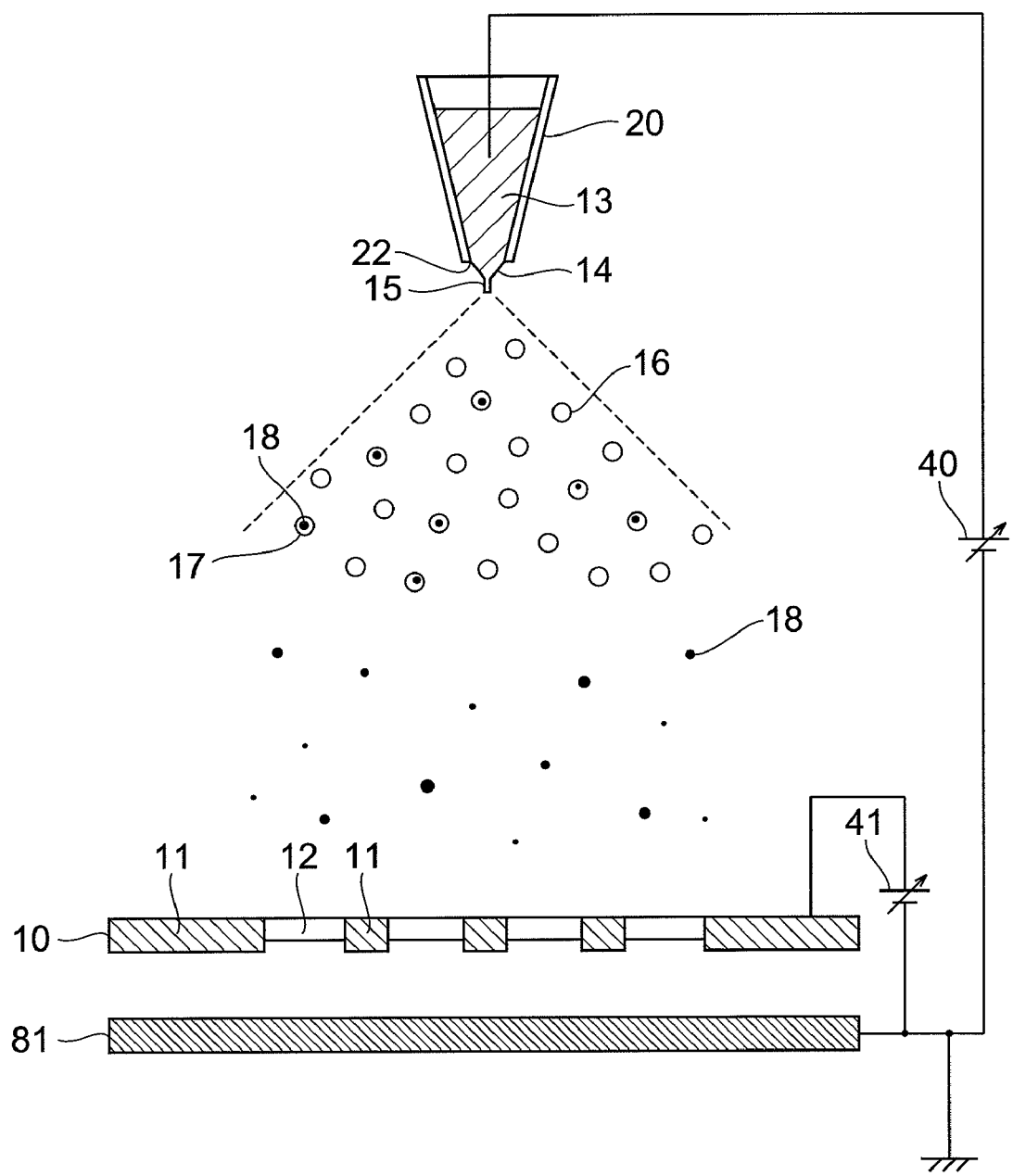

The nanomaterial immobilization conditions in the nanomaterial observation sample preparation shall now be described further. FIG. 3 is a schematic diagram of an embodiment of an observation sample preparation method according to the present invention. As mentioned above, in the dispersion liquid 13 filled in the interior of the nozzle 20, the nanomaterial 18 is in state of being dispersed in the solvent 17. Also, with the example shown in FIG. 3, the reference electrode 81 is connected to the ground potential and the bias voltage for immobilization position adjustment (a positive bias voltage in the example of FIG. 3) is applied to the grid portion 11 of the observation substrate 10.

When in this state, the electrostatic spraying voltage (a positive voltage in the example of FIG. 3) is applied to the dispersion liquid 13 inside the nozzle 20, a Taylor cone 14 with a conical liquid surface is formed from the dispersion liquid spray outlet 22 at the tip of the nozzle 20 toward the substrate 10 below. From the tip of the Taylor cone 14, the dispersion liquid 13 becomes, via a fine jet 15, a plurality of charged microdroplets 16 (positively charged microscopic droplets in the example of FIG. 3).

The charged droplets 16 of the nanomaterial dispersion liquid 13 are thereby electrostatically sprayed from the nozzle 20 at the positive potential toward the reference electrode 81 at the ground potential and the substrate 10, disposed above the reference electrode 81 and with which the bias voltage is applied to the grid portion 11 (spraying step). The electrostatic spraying of the dispersion liquid 13 is preferably performed under the condition where one or zero particles of the nanomaterial 18 are contained in each individual droplet 16 sprayed as shown in FIG. 3. In this case, a droplet 16 generated from the tip of the nozzle 20 is either a droplet containing one particle of the nanomaterial 18 or a droplet of just the solvent 17 that does not contain any of the nanomaterial 18.

With each individual droplet 16 of the dispersion liquid 13 sprayed from the spray outlet 22 of the nozzle 20, the solvent 17 contained in the droplet 16 dries and a state where just the nanomaterial 18 remains is attained in the spray atmosphere until reaching the substrate 10 from the nozzle 20 (drying step). The positively charged nanomaterial 18 in the state where the solvent 17 has dried up is then electrostatically deposited on the surface of the substrate 10, and the nanomaterial particles 18 are thereby dispersed and immobilized in a scattered state on the substrate 10 (immobilizing step).

In the electrostatic spraying of the dispersion liquid 13 and the electrostatic deposition of the nanomaterial 18, directions of lines of electric force between the nozzle 20, and the observation substrate 10 and reference electrode 81 and trajectories of the charged nanomaterial 18 are controlled by actions of the bias voltage applied to the grid portion 11. The nanomaterial immobilization positions on the substrate 10 are thereby adjusted and the nanomaterial 18 is immobilized satisfactorily on the supporting films 12 between the grid portion 11.

Effects of the nanomaterial observation sample preparation apparatus and the observation sample preparation method according to the above-described embodiment shall now be described.

With the observation sample preparation apparatus 1A and the preparation method shown in FIGS. 1 and 3, the nanomaterial observation sample is prepared by immobilizing the nanomaterial on the observation substrate 10 by applying the predetermined voltage between the nanomaterial dispersion liquid 13, filled in the interior of the electrostatic spray nozzle 20, and the substrate 10 to electrostatically spray and dry the dispersion liquid 13 and electrostatically deposit the nanomaterial 18. With this configuration, aggregation of the nanomaterial particles 18 on the substrate 10 can be suppressed in comparison, for example, to a method for coating the dispersion liquid 13 on the substrate surface.

Furthermore, in the immobilization of the nanomaterial 18, in regard to the observation substrate 10 including the conductive grid portion 11 and the supporting films 12, the substrate 10 is not directly set to the reference potential (for example, the ground potential) but the reference electrode 81 is disposed separately at the opposite side of the substrate 10 from the nozzle 20. The trajectories of the nanomaterial from the nozzle 20 toward the substrate 10 and the immobilization positions on the substrate 10 are adjusted by applying the bias voltage of the same polarity as the electrostatic spraying voltage to the grid portion 11 of the substrate 10.

Deposition of the nanomaterial on the grid portion 11 is thereby suppressed to enable the nanomaterial to be immobilized adequately on the supporting films 12, which are used for nanomaterial observation and are disposed between the grids, and a nanomaterial observation sample of satisfactory state to be prepared. Such an observation sample can be used favorably, for example, as an observation sample for TEM observation of the nanomaterial.

Figure 4:
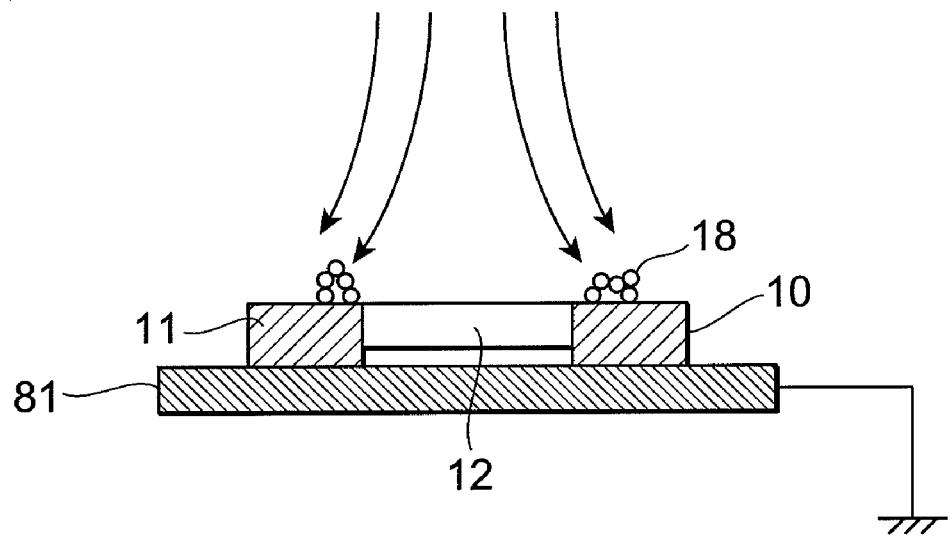
Figure 4:
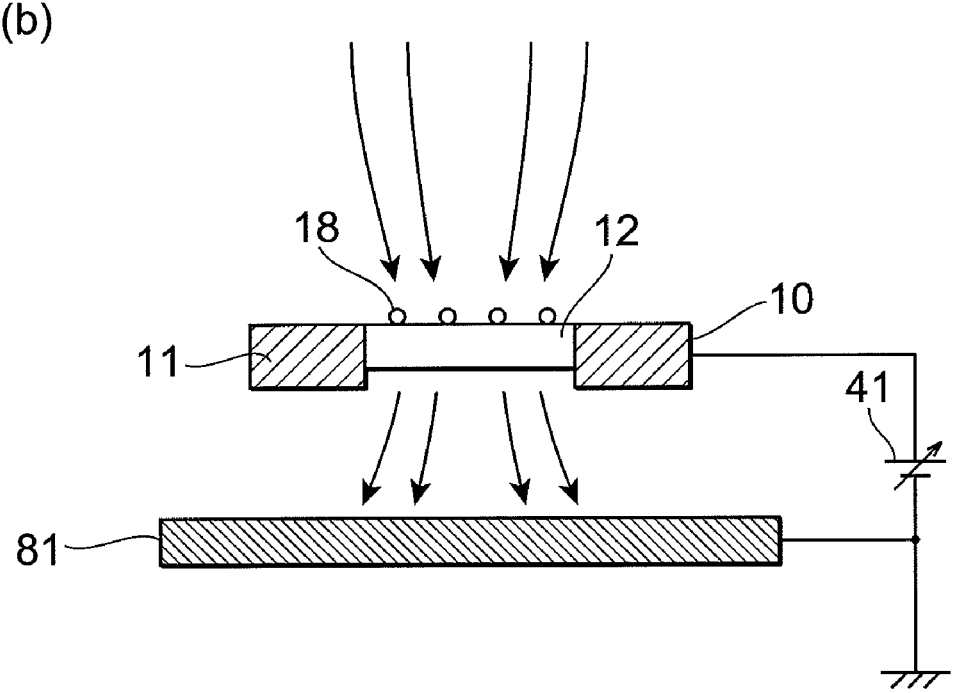

The adjustment of the above-described nanomaterial immobilization positions shall now be described with reference to FIG. 4. In a case where the grid portion 11 of the substrate 10 is connected to the reference electrode 81 and set to the ground potential, as shown schematically by arrowed lines in (a) in FIG. 4, the lines of electric force from the nozzle 20 to the substrate 10 concentrate at edges of the conductive grid portion 11. In this case, much of the charged nanomaterial 18 is electrostatically deposited on the grid portion 11 along the lines of electric force and the nanomaterial 18 is not adequately immobilized on the supporting films 12 used for observation.

On the other hand, in a case where the reference electrode 81 is spaced apart from and disposed below the observation substrate 10 and the bias voltage is applied to the grid portion 11 of the substrate 10, as shown in (b) in FIG. 4, the lines of electric force pass through the supporting films 12 and are directed toward the reference electrode 81 below. In this state, the charged nanomaterial 18 is deposited along the lines of electric force and on the supporting films 12, and a nanomaterial observation sample of satisfactory state is thereby obtained.

Here, as the observation substrate 10 on which the nanomaterial is immobilized, any of various specific configurations may be used. In general, a substrate, including the conductive grid portion 11 having the mesh-like form with one or a plurality of openings and the supporting films 12 disposed at the openings of the grid portion 11 as described above, is used. As such a substrate, a substrate having a grid portion 11 made of copper and having a diameter of 3 mmϕ, a thickness of 25 μm, a mesh width of 30 μm, and a single mesh pitch interval of 150 μm can be cited as an example of a general metal mesh substrate for TEM observation.

In regard to a setting value of the bias voltage for immobilization position adjustment that is applied between the grid portion 11 of the observation substrate 10 and the reference electrode 81, the absolute value thereof (a magnitude of the voltage) is preferably set to be in a range of 5V to 50V. Electrostatic spraying of the nanomaterial dispersion liquid 13 from the nozzle 20 to the substrate 10 and adjustment of the nanomaterial trajectories and the immobilization positions on the substrate 10 can thereby be combined favorably.

Specifically, when the bias voltage is too low, the effect of adjustment of the nanomaterial immobilization positions cannot be obtained adequately. Based on this point, the bias voltage is preferably set to not less than 5V. Also, when the bias voltage is too high, it becomes difficult for the charged nanomaterial to approach the substrate 10 due to electrostatic repulsion and immobilization of the nanomaterial on the substrate 10 cannot be performed favorably. Based on this point, the bias voltage is preferably set to not more than 50V.

In regard to the application of the bias voltage to the grid portion 11 of the substrate 10, the bias electrode 83, spaced apart from the reference electrode 81 and electrically connected to the grid portion 11 of the substrate 10, is provided and the bias voltage from the adjustment voltage applying device 41 is applied to the grid portion 11 via the electrode 83 in the configuration shown in FIG. 1. The bias voltage for immobilization position adjustment can thereby be applied favorably to the conductive grid portion 11. However, in regard to the application of the bias voltage, the voltage may instead be applied directly to the grid portion 11 from the adjustment voltage applying device 41.

In a case where the bias electrode 83 is provided in addition to the reference electrode 81 as described above, it is preferable to use the voltage application jig 80, in which the reference electrode 81, the bias electrode 83, and the insulating layer 82 between the electrodes are integrally configured as shown in FIG. 1. With this configuration, installation, connection, etc., of the reference electrode 81 and the bias electrode 83 with respect to the observation substrate 10 is facilitated.

The configuration using the jig 80 is also effective in terms of handling of the respective electrodes 81 and 83 and the observation substrate 10, etc. For example, in a case where the metal mesh substrate of 3 mmϕ diameter illustrated above is used as the observation substrate 10, because such a substrate is not strong mechanically, it is difficult to provide electrical contact for applying the bias voltage to the grid portion 11. Meanwhile, by using the voltage application jig 80 with the above-described configuration, an adequate mechanical strength can be secured to favorably realize support of the observation substrate 10 and application of the bias voltage to the grid portion 11.

Also, with the configuration shown in FIG. 1, the reference electrode 81 is disposed so as to include the positions opposing the supporting films 12 of the substrate 10, and the opening 85 is formed in the insulating layer 82 and the bias electrode 83 to provide an arrangement enabling the reference electrode 81 to be in view from the supporting film 12. Control of the lines of electric force and the nanomaterial trajectories by application of the bias voltage to the grid portion 11 (see FIG. 4) and adjustment of the nanomaterial immobilization positions on the substrate 10 can thereby be realized favorably. For example, when the metal mesh substrate of 3 mmϕ diameter is used as the observation substrate 10, a gap of approximately 2 mm width that can be spanned by the substrate 10 can be employed as the opening 85. Such a configuration is also effective in terms of enabling the observation substrate 10 to be recovered by tweezers, etc., after end of the sample preparation process.

Furthermore, in regard to specific conditions of the sample preparation, in the example shown in FIG. 3, in the electrostatic spraying of the dispersion liquid 13 from the nozzle 20 onto the substrate 10, the spraying of the dispersion liquid 13 is performed under the condition where one or zero particles of the nanomaterial 18 are contained in each individual droplet 16. By thus spraying the dispersion liquid 13 so that at most one particle of the nanomaterial is contained in each individual droplet sprayed, the nanomaterial 18 contained in the droplet 16 is prevented from forming an aggregate in the process of drying of the solvent 17. The nanomaterial can thus be immobilized favorably in an adequately dispersed state on the nanomaterial supporting films 12 of the observation substrate 10.

Also, in the above-described preparation method, with each individual droplet 16 of the dispersion liquid 13 sprayed from the nozzle 20, the solvent 17 contained in the droplet 16 is dried in the spray atmosphere, and the nanomaterial 18 is electrostatically deposited on the surface of the substrate 10 in a solvent-dried state to immobilize the nanomaterial on the substrate 10. The nanomaterial contained in each individual droplet sprayed from the nozzle 20 can thereby be immobilized favorably on the surface of the observation substrate 10.

Such spraying conditions, drying conditions, and immobilization conditions in nanomaterial immobilization can be realized by appropriately setting and adjusting such conditions as the configuration, shape, and size of the electrostatic spray nozzle 20, the nanomaterial concentration in the dispersion liquid 13, the distance between the nozzle 20 and the substrate 10, the value of the electrostatic spraying voltage applied to the dispersion liquid 13, the value of the bias voltage, a diameter of each droplet sprayed from the nozzle 20. Also, in regard to the electrostatic spraying voltage and the bias voltage, the abovementioned conditions may be realized by controlling the applied voltages by the controller 45 that functions as the voltage controller as described above.

The specific conditions of the nanomaterial observation sample preparation process using the observation sample preparation apparatus 1A of the above-described configuration are not restricted to those of the above-described example, and the preparation process can be carried out under various conditions. For example, in regard to the nanomaterial contained in a droplet sprayed from the nozzle 20, electrostatic spraying of the dispersion liquid may be performed under conditions where two or more particles of the nanomaterial are contained. These conditions are preferably set appropriately according to the required conditions of nanomaterial immobilization on the substrate.

Figure 5:
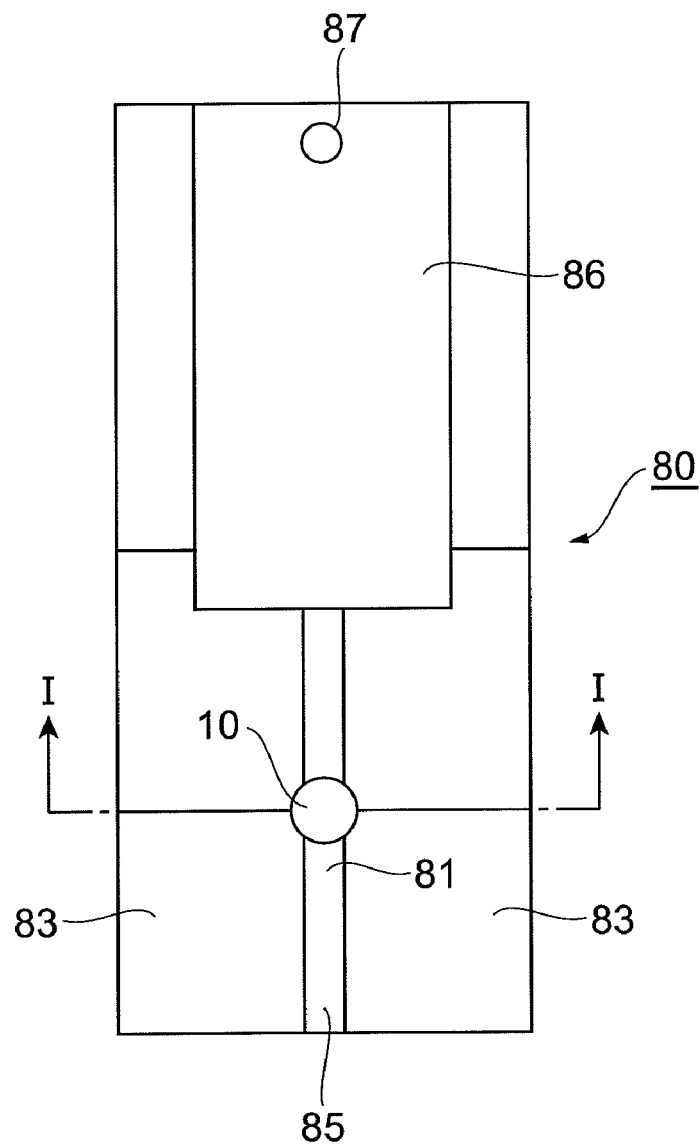
Figure 5:
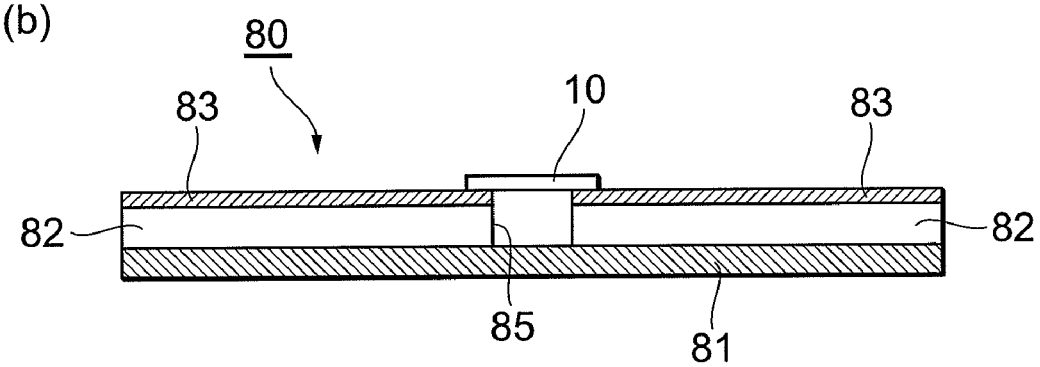

FIG. 5 shows diagrams of a specific example of a configuration of the voltage application jig 80 used in the preparation apparatus 1A shown in FIG. 1, (a) in FIG. 5 is a plan view and (b) in FIG. 5 is a sectional view taken on arrows I-I. The jig 80 of the present configuration example is configured by laminating insulating layers 82, each made of a glass substrate, and ITO electrodes 83, which are the bias electrodes, on a Si substrate that functions as the reference electrode 81.

The insulating layers 82 and the bias electrodes 83 are disposed at left and right sides in the figure and an interval in between is a groove-like structure that serves as the opening 85. Thus, in regard to the opening 85 of the jig 80, any of various specific configurations, such as a groove-like structure, hole-like structure may be employed. A shared voltage supplying electrode 86 made of copper foil tape is connected to the left and right bias electrodes 83 and the bias voltage is supplied to the bias electrodes 83 via the electrode 86 and a terminal 87. A state in which the observation substrate 10 is set on the jig 80 is shown in FIG. 5.

Figure 6:
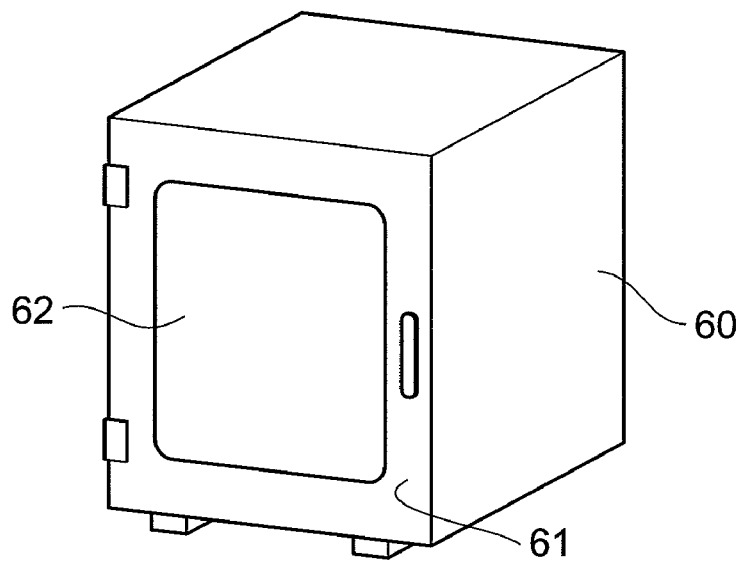
Figure 6:
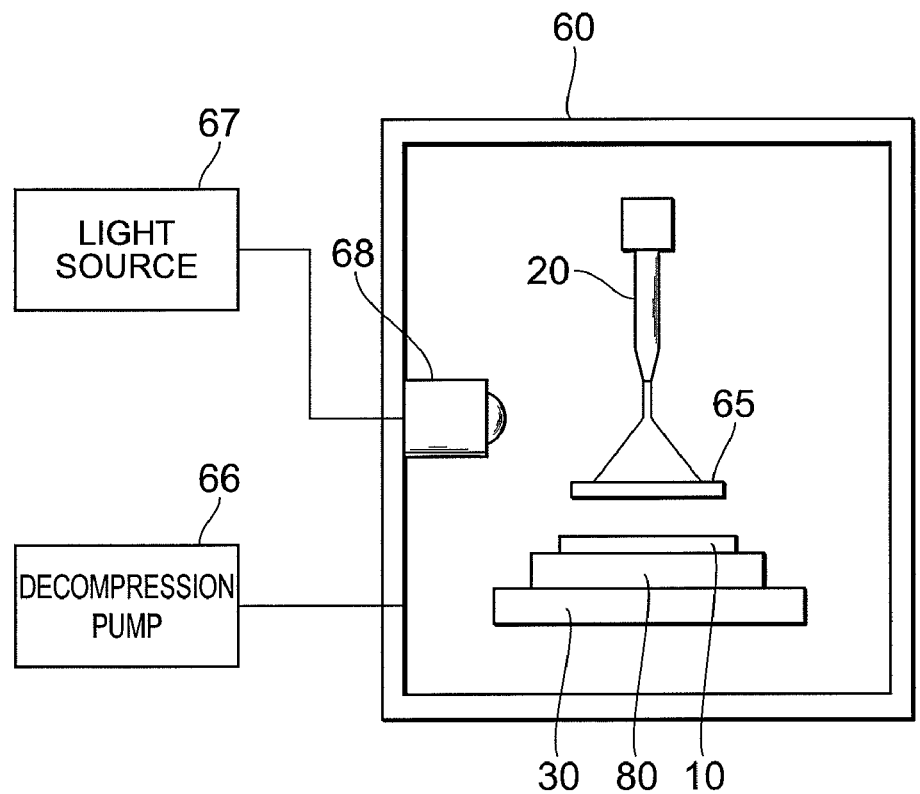

If, in regard to the spraying of the dispersion liquid 13 from the nozzle 20 to the substrate 10, the spray atmosphere must be adjusted and controlled, a spray chamber 60, housing the nozzle 20, the substrate stage 30, etc., may be configured as shown schematically in FIG. 6. In this case, a type of gas to be the atmosphere in performing the nanomaterial sample preparation process inside the spray chamber 60 or a pressure of the gas, etc., can be set appropriately. As a specific configuration example, (b) in FIG. 6 shows a configuration in which a decompression pump 66 is connected to the spray chamber 60.

With the configuration shown in (a) in FIG. 6, an observation window 62 is provided on a door 61 of a front face of the spray chamber 60, and the observation window 62 is made up of a Fresnel lens or other magnifying lens. With this configuration, the sample preparation process executed in the interior of the spray chamber 60 can be observed and checked readily. With the configuration shown in FIG. 6(b), an illumination 68, using a cold light source 67, is disposed in the interior of the spray chamber 60 for observation, etc., of the sample preparation process. Also, a spray shutter 65 that switches between execution and non-execution of electrostatic spraying may be disposed inside the spray chamber 60 and between the nozzle 20 and the substrate 10.

The configuration of the electrostatic spray nozzle 20 used for spraying of the dispersion liquid in the preparation apparatus 1A shown in FIG. 1 shall now be described. As the nozzle 20, the configuration having the tubular nozzle body 21 employing a glass capillary, etc., as described above can be used favorably. In regard to the nozzle body 21 of nozzle 20, an inner diameter at a tip of the tubular structure is preferably not more than 50 μm.

By thus making the inner diameter of the nozzle body 21 and the nozzle bore diameter at the spray outlet 22 adequately small, it becomes possible to make microdroplets of the dispersion liquid 13 sprayed from the nozzle 20 adequately small, that is, for example, to form microdroplets of submicron order favorable for electrostatic spraying of a nanomaterial having a diameter not more than 100 nm and reliably suppress aggregation of the nanomaterial in the droplets. In regard to the inner diameter at the tip of the nozzle body 21, it is more preferable to make the inner diameter not more than 20 μm. In consideration of preparation techniques (for example, glass processing techniques) for preparing the nozzle 20, the inner diameter at the tip of the nozzle body 21 is preferably not less than 3 μm.

Figure 7:
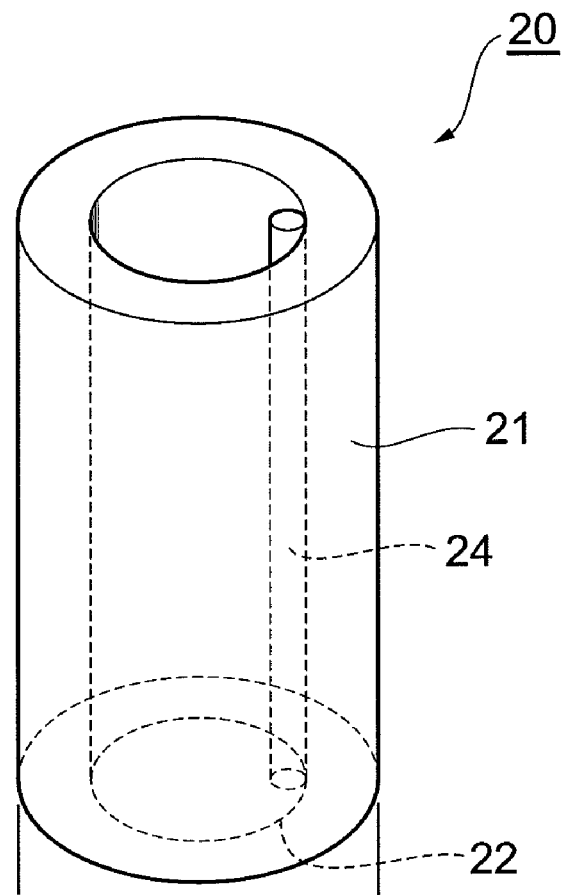
Figure 7:
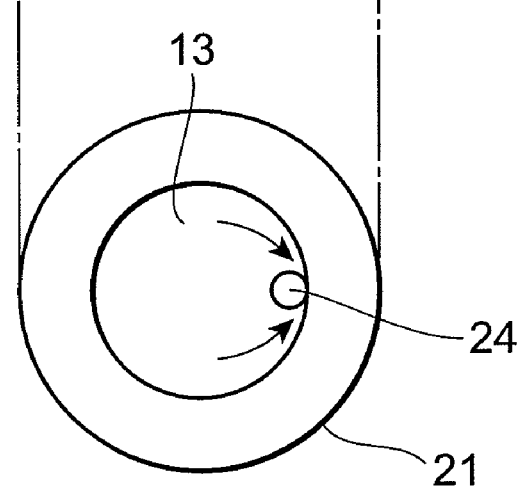

As another example of a configuration of the nozzle 20, a configuration where a core structure is disposed in an interior of a tubular nozzle body may be employed. FIG. 7 shows enlarged views of a configuration of a tip of a modification example of the electrostatic spray nozzle 20, with (a) in FIG. 7 being a perspective view of the tip of the nozzle 20 as viewed from a side surface side, and (b) in FIG. 7 being a sectional view of the nozzle 20. In the present modification example, a rod-like core structure 24 is disposed in the interior of the nozzle body 21. The core structure 24 is disposed so as to extend along the direction of the longitudinal axis of the nozzle body 21 in a state of contacting an inner wall of the nozzle body 21. Such a core structure 24 is fixed, for example, by fusion bonding to the inner wall of the nozzle body 21.

With this configuration, the dispersion liquid 13 tends to enter into the gap between the inner wall of the nozzle body 21 and the core structure 24 by a capillary action as indicated by arrows in FIG. 7(b). Consequently, the dispersion liquid 13 is supplied reliably to the tip of the nozzle body 21. The core structure 24 is preferably disposed to extend in a predetermined range extending along the longitudinal direction of the nozzle body 21 and including the spray outlet 22 (for example, to extend across an entire length of the nozzle body 21). Such a nozzle 20 can be prepared using, for example, a glass capillary and a glass rod.

With the nozzle 20 having the core structure 24, even when the tip of the nozzle body 21 is made narrow in diameter, the dispersion liquid 13 is reliably supplied to the tip where the spray outlet 22 is disposed by the capillary action between the inner wall of the nozzle body 21 and the core structure 24. Occurrence of nozzle clogging due to solids or air bubbles, etc., in the interior of the nozzle body 21 is thereby prevented. Also, the nanomaterial sample preparation process can be executed efficiently without having to lower the nanomaterial concentration in the dispersion liquid 13.

That is, with the configuration provided with the core structure 24, even when drying of the solvent occurs at the tip of the nozzle 20, the liquid surface of the dispersion liquid 13 is maintained by natural supplying of the solvent to the tip along the core structure 24. By the drying of the solvent at the tip of the nozzle 20 thus being suppressed, formation of solids that cause nozzle clogging is prevented. Also, even when an air bubble is generated in the interior of the nozzle body 21, because the solvent is naturally supplied to the tip of the nozzle 20 by flowing along the core structure 24 and around the air bubble, occurrence of nozzle clogging due to the air bubble is prevented.

Also, in regard to the electrostatic spraying of the dispersion liquid 13, by the application of the voltage between the dispersion liquid 13 and the substrate 10 as shown in FIG. 3, the liquid surface of the Taylor cone 14 and the jet 15 are formed below the spray outlet 22 and the dispersion liquid 13 is sprayed by the formation of the plurality of charged microdroplets 16. In this process, sizes of the jet 15 and the droplet 16 are influenced by an electrostatic force directed toward the substrate 10 and a surface tension directed toward the nozzle 20. Meanwhile, with the nozzle 20 having the core structure 24, in addition to the electrostatic force directed toward the substrate 10 and the surface tension directed toward the nozzle 20, a capillary force due to the core structure 24 acts as a force directed toward the nozzle 20 in a manner similar to the surface tension. The sizes of the jet 15 and the droplet 16 are thereby made small in comparison to the case where the core structure 24 is not provided.

The core structure 24 preferably has a diameter in a range of 0.1 times to 0.2 times the inner diameter of the nozzle body 21. In this case, the flow path for the dispersion liquid 13 inside the nozzle body 21 can be combined favorably with the core structure 24 and the dispersion liquid 13 can be supplied favorably by the capillary action to the spray outlet 22 at the tip. For example, in a case where the inner diameter of the nozzle body 21 is 20 µm, the diameter of the core structure 24 is preferably set in a range of 2 µm to 4 µm.

Figure 8:
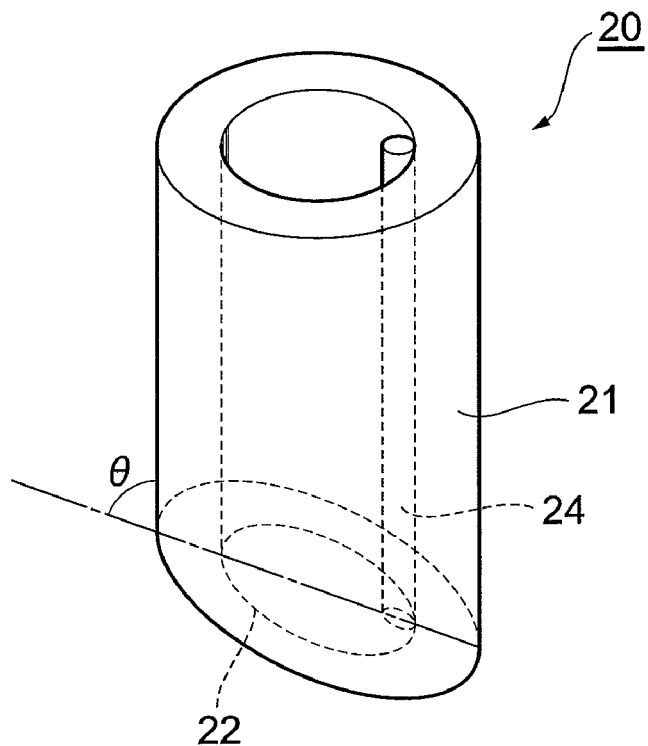
Figure 8:
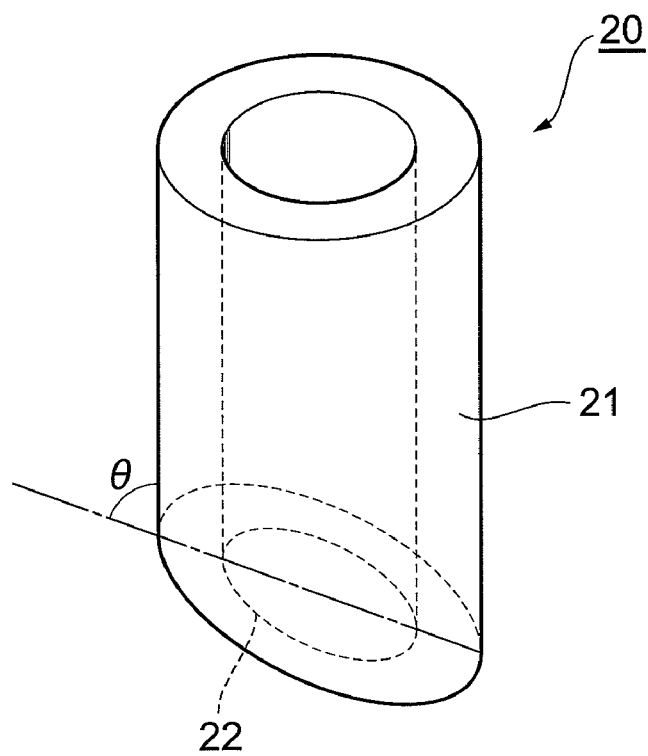
Figure 9:
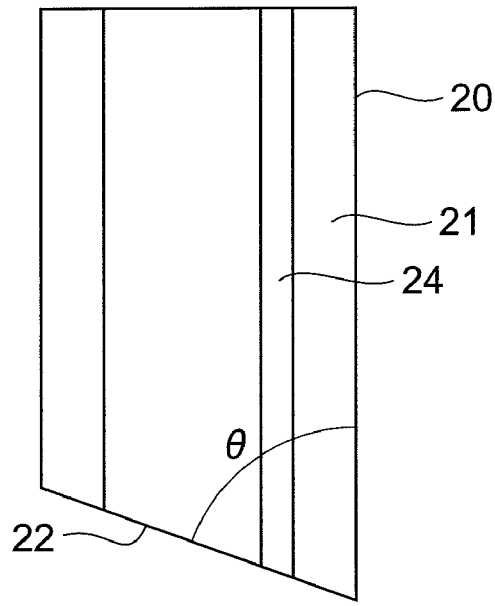
Figure 9:
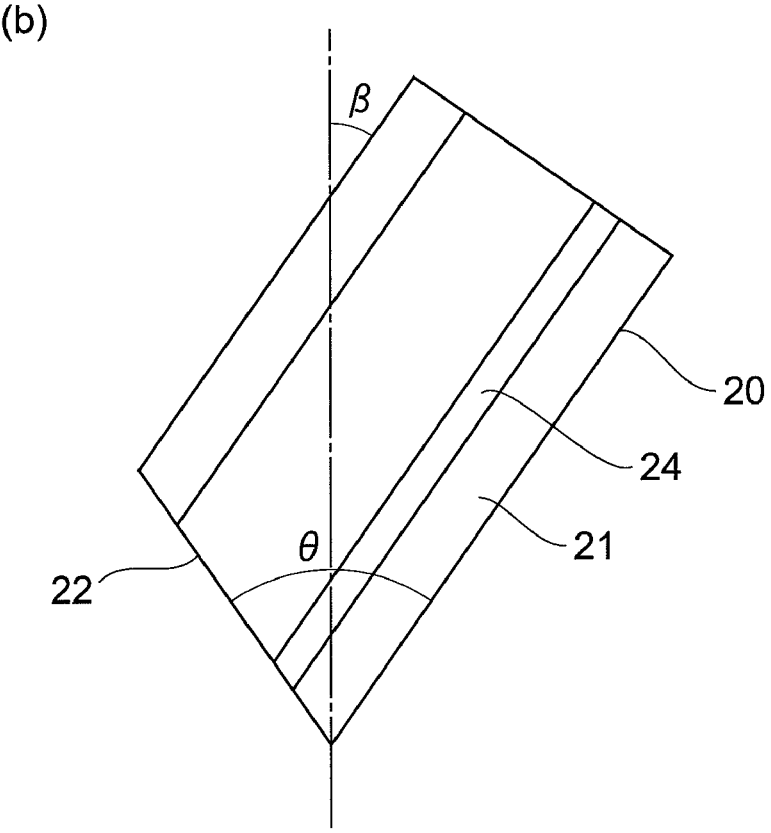

In regard to the specific configuration of the electrostatic spray nozzle 20, although in the above-described configuration example, a tip surface of the nozzle body 21 forming the spray outlet 22 is a surface perpendicular to the longitudinal axis, the nozzle body 21 may, as in another modification example of the configuration of the tip of nozzle 20 shown in a perspective view in (a) in FIG. 8 and a sectional view in (a) in FIG. 9, have an acute angle shape where the spray outlet 22 is inclined at a predetermined angle θ so as to form an acute angle with respect to the longitudinal axis of the tubular structure.

When the nozzle body 21 has such an acute angle shape, a flow path narrower than the inner diameter of the nozzle body 21 is formed at the tip portion and a high electric field for electrostatic spraying concentrates at the tip portion. The droplets of the dispersion liquid 13 formed in the spraying process can thereby be made even smaller. In regard to the angle θ, which the spray outlet 22 forms with respect to the longitudinal axis of the nozzle body 21 (the angle formed by a side surface and the tip surface of the nozzle body 21, see FIG. 9(a)) in such an acute angle shape, the inclination angle θ is preferably set in a range of 45° to 70°.

Also, in the above configuration, the core structure 24 in the interior of the nozzle body 21 is preferably positioned at the tip side of the acute angle at the spray outlet 22 and disposed so as to extend upward from the tip of the acute angle shape as shown in FIG. 8(a). The dispersion liquid 13 can thereby be reliably supplied to the tip of the acute angle shape that is the tip of the flow path of the dispersion liquid 13 in the interior of the nozzle body 21. However, in regard to the core structure 24, any of various specific configurations may be employed, such as disposing the core structure 24 at a position shifted by just a predetermined distance from the tip of the acute angle of the nozzle body 21.

Also, in the case where the nozzle body 21 has the acute angle shape, as shown in (b) in FIG. 9, electrostatic spraying of the dispersion liquid 13 onto the substrate 10 may be performed with the nozzle 20 being installed so that the longitudinal axis of the nozzle body 21 is in a state of being inclined at an installation angle β toward the tip side of the acute angle shape with respect to the nanomaterial spraying axis. With this configuration, even if an opening area of the elliptical spray outlet 22 of the nozzle body 21 is large, an area of the spray outlet 22 as viewed from the substrate 10 can be made small to reliably make small the dispersion liquid microdroplets formed during spraying.

In this case, in regard to the installation angle β of the nozzle 20, the installation angle β is set in a range of preferably θ/4 to 3θ/4 with respect to the angle θ of the acute angle shape of the nozzle body 21 and especially preferably, the installation angle is set so that β=θ/2. In a case where increase of the opening area of the spray outlet 22 of the nozzle body 21, etc., does not present a problem, β may be set to 0° so that the nanomaterial spraying axis and the longitudinal axis of the nozzle body 21 are matched as shown in FIG. 9(a).

The configuration where the nozzle body 21 has the acute angle shape can also be applied in a likewise manner to the nozzle 20 that is not provided with the core structure 24 (see FIG. 1) as shown in (b) in FIG. 8. Even in this configuration, the droplets of the dispersion liquid 13 formed during spraying can be made even smaller by the effect of the acute angle shape. The configuration of incliningly positioning the nozzle body 21 with respect to the nanomaterial spraying axis can likewise be applied to the nozzle 20 that is not provided with the core structure 24.

Figure 10:
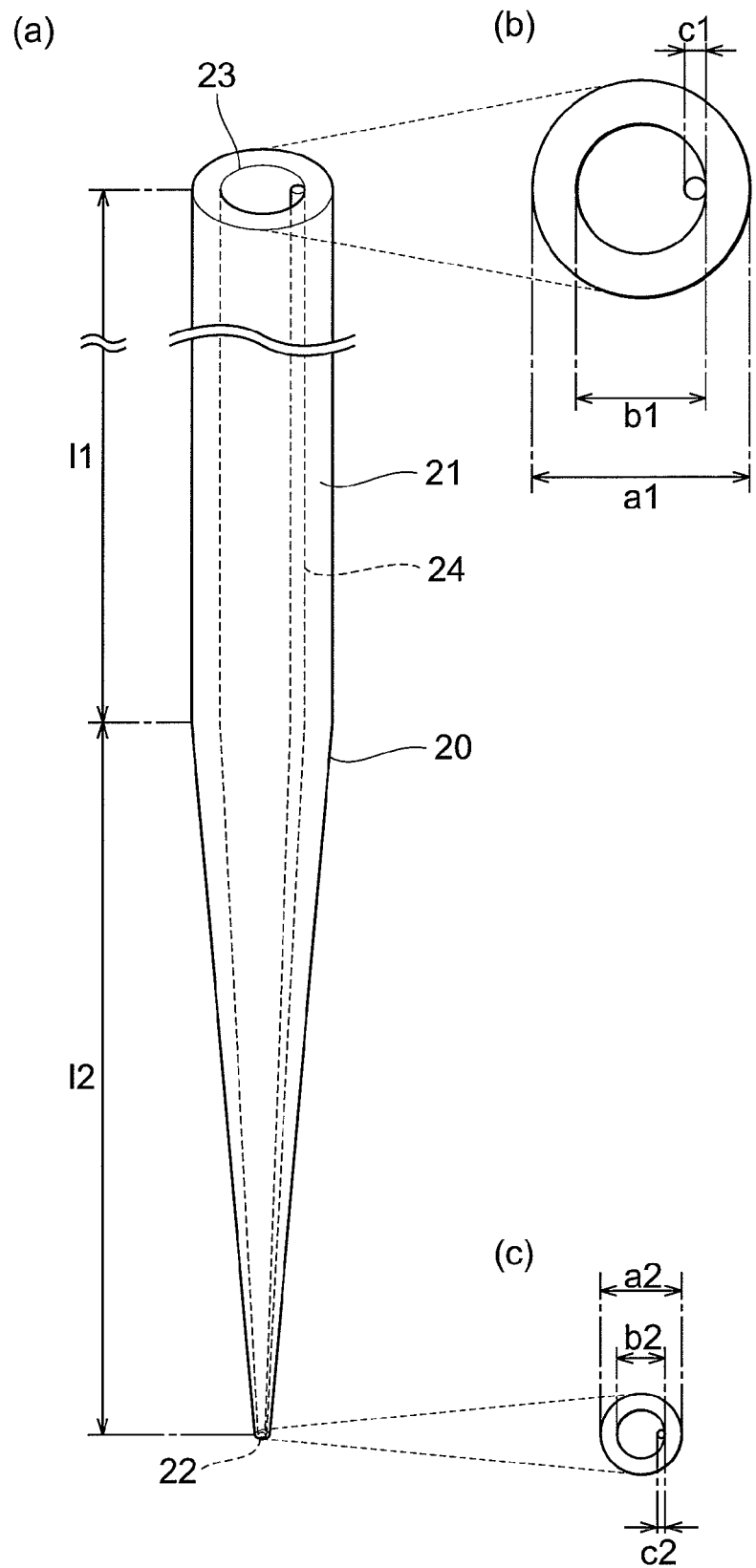

FIG. 10 shows diagrams of a specific example of the configuration of the electrostatic spray nozzle 20. The nozzle 20 according to the present configuration example is formed using a tubular glass capillary as the nozzle body 21, using a glass rod, disposed in a state of contacting the inner wall in the interior of the glass capillary, as the core structure 24, and making one end narrow in diameter by glass processing. Of the openings 22 and 23 at the respective ends of the tubular nozzle body 21, the opening 22 at the narrowed end side is the dispersion liquid spray outlet.

In the nozzle 20 shown in (a) in FIG. 10, an opening 23 side portion at the upper end is a wide diameter portion having a fixed diameter. A dispersion liquid spray outlet 22 side portion at the lower end is a narrow diameter portion that decreases in diameter toward the tip. The shape of the upper wide diameter portion (see (b) in FIG. 10) is specifically such that, for example, a length of the wide diameter portion is l1=60 mm, an outer diameter of the nozzle body 21 is a1=1 mm, the inner diameter is b1=0.6 mm, and the diameter of the core structure 24 is c1=0.1 mm.

Meanwhile, the shape of the lower narrow diameter portion (see (c) in FIG. 10) is specifically such that, for example, a length of the narrow diameter portion is l2=5 mm, and at a lower end of the narrow diameter portion, the outer diameter of the nozzle body 21 is a2=20 μm, the inner diameter is b2=12 μm, and the diameter of the core structure 24 is c2=2 μm. For example, when an aqueous dispersion liquid of titanium oxide with an average particle diameter of 50 nm and a concentration of 0.1% is used as the dispersion liquid 13, the nanomaterial immobilization process can be executed satisfactorily using the nozzle 20 with which the nozzle inner diameter at the tip is 12 μm and under the conditions of the distance between the nozzle 20 and the substrate 10 being 20 mm and the electrostatic spraying voltage applied to the dispersion liquid 13 being 1400V. In general, the distance between the nozzle 20 and the substrate 10 is preferably set to a distance in a range of 5 mm to 30 mm. The electrostatic spraying voltage is preferably set to a voltage not more than 5000V.

Introduction of the nanomaterial dispersion liquid 13 into the electrostatic spray nozzle 20 shall now be described. As mentioned above, the introduction of the dispersion liquid 13 into the interior of the tubular nozzle body 21 is performed, according to the specific configuration, etc., of the preparation apparatus 1A, from the opening 23 at the upper end of the nozzle body 21 or from the spray outlet 22 at the lower end. Particularly, in regard to the introduction of the dispersion liquid 13, it is preferable to introduce the dispersion liquid 13 into the nozzle body 21 from the spray outlet 22 at the lower side. In this case, it becomes possible to reliably supply the dispersion liquid 13 to the tip at which the spray outlet 22 is disposed in the interior of the nozzle body 21. Also, the nozzle 20 can be filled with a minute amount of the dispersion liquid 13 in a simple manner.

Figure 11:
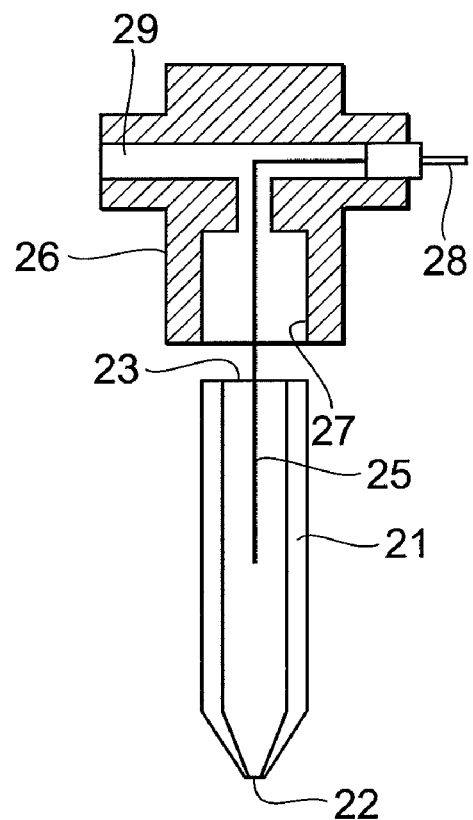
Figure 11:
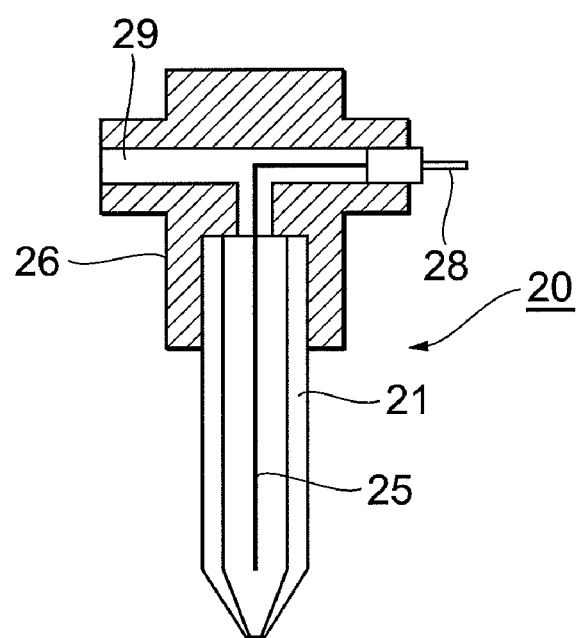

A specific example of a method for introducing the nanomaterial dispersion liquid 13 into the nozzle 20 and a modification example of the nozzle 20 shall now be described using FIG. 11. FIG. 11 shows diagrams of a modification example of the configuration of the electrostatic spray nozzle. The nozzle 20 according to the present configuration example includes a nozzle holder 26 in addition to the nozzle body 21. Here, (a) in FIG. 11 shows a state before the nozzle body 21 is mounted on the holder 26, and (b) in FIG. 11 shows a state where the electrostatic spray nozzle 20 is assembled by mounting the nozzle body 21 on the holder 26.

The nozzle holder 26 is connected to the opening 23 of the nozzle body 21 and supports the nozzle body 21. Specifically, the nozzle holder 26 of the present configuration example includes a nozzle body fixing portion 27, a voltage supplying terminal 28, and a negative pressure inlet 29. The nozzle body fixing portion 27 has a recessed shape at a lower portion of the holder 26, and as shown in FIG. 11(b), the nozzle body 21 is fixed to the holder 26 by its upper end being inserted into the fixing portion 27. The nozzle holder 26 is thus enabled to be detachably attached to the nozzle body 21. The voltage supplying terminal 28 is connected to the electrode 25, made from a metal wire, etc. (see FIG. 1), and the spraying voltage applying device 40 supplies the electrostatic spraying voltage to the electrode 25 and the dispersion liquid 13 via the terminal 28.

The negative pressure inlet 29 is for applying a negative pressure to the interior of the tubular nozzle body 21 and is used to introduce the dispersion liquid 13 into the interior of the nozzle body 21 from the dispersion liquid spray outlet 22 as described above. The negative pressure inlet 29 is spatially connected to the interior of the nozzle body 21 in the state where the nozzle body 21 is fixed to the holder 26.

With the method for introducing the dispersion liquid 13 using the holder 26, first, the tip of the nozzle body 21 is immersed in the dispersion liquid 13 contained in a container. Then, by depressurizing the interior of the nozzle body 21 from the negative pressure inlet 29 and putting the interior in a negative pressure state, the liquid level of the dispersion liquid 13 is made to rise from the spray outlet 22 side in the nozzle body 21. A necessary amount of the dispersion liquid 13 is thereby filled into the nozzle 20 from the spray outlet 22 and a state where the dispersion liquid 13 contacts the electrode 25 is realized. With the nozzle 20 of this configuration, when the dispersion liquid 13 is introduced from the spray outlet 22 side, the dispersion liquid 13 fills only the interior of the nozzle body 21 and a merit that washing of the holder 26 and other work is made unnecessary is provided.

Figure 12:
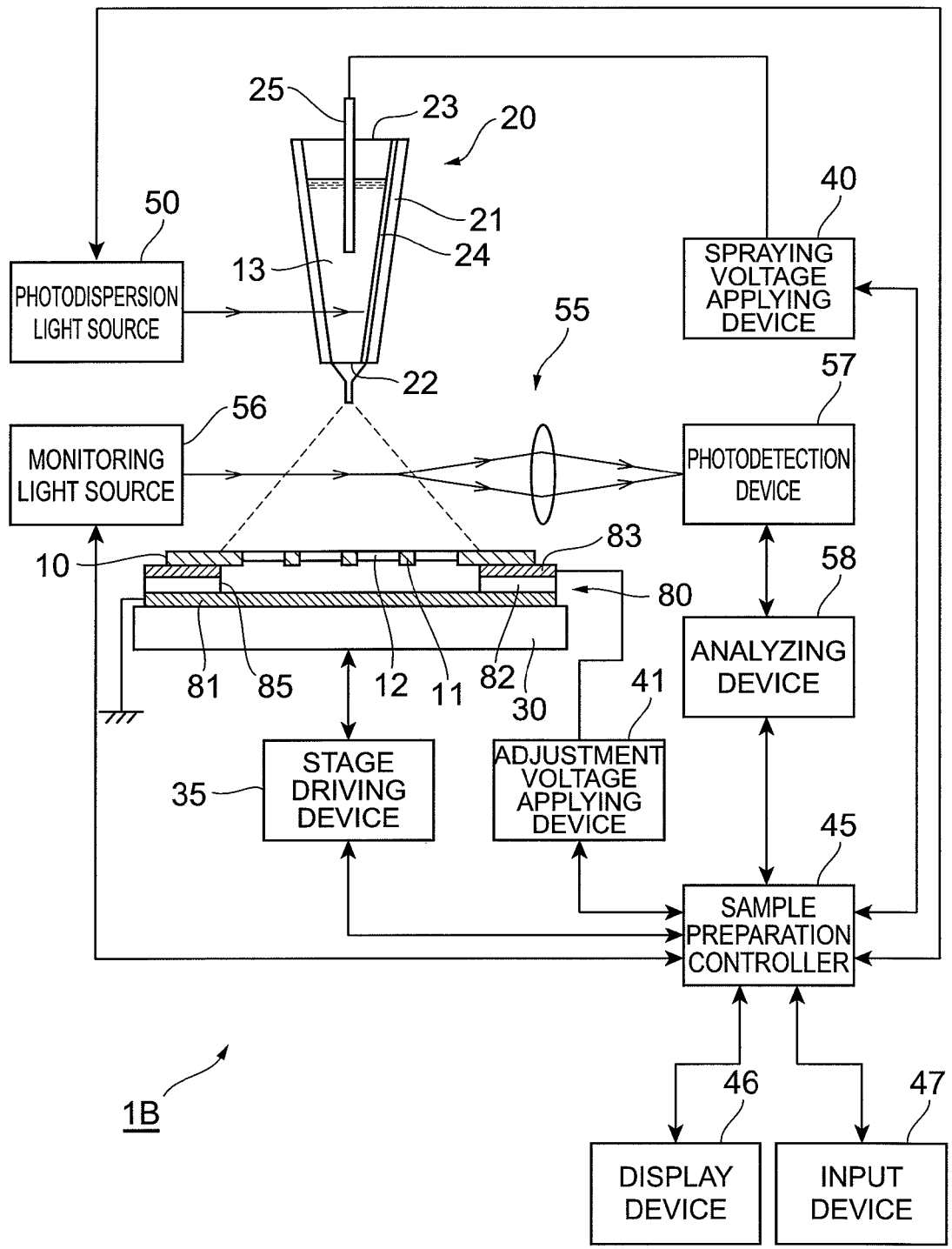

FIG. 12 is a schematic block diagram of a configuration of a second embodiment of an observation sample preparation apparatus according to the present invention. In regard to the substrate stage 30 on which the observation substrate 10 is set, the voltage application jig 80, the stage driving device 35, the spraying voltage applying device 40, and the adjustment voltage applying device 41, the configuration of the preparation apparatus 1B according to the present embodiment is the same as that of the preparation apparatus 1A shown in FIG. 1. Also, with the present embodiment, a configuration including the nozzle body 21 and the core structure 24 is illustrated as the electrostatic spray nozzle 20. However, the nozzle 20 excluding the core structure 24 as in FIG. 1 may be employed in the present configuration as well.

The observation sample preparation apparatus 1B shown in FIG. 12 includes a photodispersion laser light source 50 irradiating the dispersion liquid 13 in the interior of the nozzle body 21 with photodispersion laser light for dispersing aggregated nanomaterial. With this configuration, even if the nanomaterial that is dispersed in the solvent aggregates in the dispersion liquid 13 before electrostatic spraying, the nanomaterial can be redispersed in the solvent of the dispersion liquid 13 by irradiation of the photodispersion laser light (photodispersing step).

The dispersion liquid 13 can thereby be electrostatically sprayed in a state where the nanomaterial is adequately dispersed in the solvent, and aggregation of the nanomaterial immobilized on the substrate 10 can be suppressed even more reliably. In regard to such a nanomaterial dispersion process by irradiation of laser light, the dispersion process may be performed by irradiating the dispersion liquid 13 prepared in a predetermined container with the laser light in a stage before filling the nozzle 20 with the nanomaterial dispersion liquid 13.

As the laser light used for photodispersion of the nanomaterial in the dispersion liquid 13, for example, pulsed laser light of a wavelength of 350 nm to 1100 nm can be used favorably. Although a laser light intensity in this case differs according to the irradiation wavelength of the laser light or absorbance characteristics, etc., of the nanomaterial dispersion liquid 13 subject to the process, for example with nanosecond-order, pulsed laser light, the irradiation intensity is preferably set to 0.01 to 50 $J/cm^2$·pulse. As a specific photodispersion laser light source 50, for example, a YAG pulsed laser light source (wavelength: 1064 nm, 532 nm, 355 nm) can be used.

Also, with the preparation apparatus 1B of FIG. 12, an aggregation state monitoring unit 55 is provided that optically monitors the aggregation state of the nanomaterial in the passage region of the charged nanomaterial. With this configuration, by optically monitoring, between the spray outlet 22 of the nozzle 20 and the substrate 10, the aggregation state of the nanomaterial, which is sprayed from the nozzle 20 and with which the solvent is dried in the atmosphere, the aggregation state of the nanomaterial immobilized on the substrate 10 can be evaluated in real time during execution of the sample preparation process (aggregation state monitoring step).

Specifically, with the configuration example shown in FIG. 12, the aggregation state monitoring unit 55 includes a monitoring light source 56, irradiating the nanomaterial passage region with monitoring light, and a photodetection device 57, detecting at least one of either scattered light or fluorescence generated from the nanomaterial due to the monitoring light. The aggregation state of the charged nanomaterial sprayed toward the substrate 10 from the nozzle 20 can thereby be monitored favorably in the passage region.

Furthermore, with the configuration example shown in FIG. 12, a detection signal, indicating a result of detection of light from the nanomaterial by the photodetection device 57, is input into an analyzing device 58, and evaluation of the aggregation state of the nanomaterial is performed in the analyzing device 58. The sample preparation controller 45, functioning as the voltage controller, references the aggregation state monitoring results input from the analyzing device 58 and controls the electrostatic spraying voltage applied between the dispersion liquid 13 and the substrate 10 by the voltage applying device 40 (voltage controlling step). The conditions of electrostatic spraying of the dispersion liquid 13 can thereby be feedback controlled favorably and automatically. Such control of the electrostatic spraying voltage may be configured to be performed manually while referencing the monitoring results by an operator.

As the monitoring light used to monitor the nanomaterial aggregation state, for example, continuous light of a wavelength of 400 nm to 700 nm can be used favorably. As the monitoring light source 56, a light source capable of focusingly irradiating the passage region of the nanomaterial sprayed from the nozzle 20 with the monitoring light is preferable. As such a light source, a laser light source, a semiconductor laser light source, an LED light source, etc., can be cited.

In regard to the scattered light from the nanomaterial, forward scattered light, side scattered light, backward scattered light, or a combination of these is preferably measured. Especially, in a case of a nanomaterial of a size of approximately several dozen nm, the aggregation state can be monitored favorably by measuring the backward scattered light. In a case of a nanomaterial of a size not more than 10 nm, the aggregation state can be monitored favorably by measuring fluorescence generated based on a quantum effect of the nanomaterial. In the monitoring of the aggregation state, it is preferable to acquire reference data in advance using a dispersion liquid that is extremely low in concentration and is considered to be in a well-dispersed state of the nanomaterial and to evaluate the nanomaterial aggregation state by comparing the reference data with actual measurement data.

For example, in aggregation state monitoring using forward scattered light from the nanomaterial, when the nanomaterial is in a well-dispersed state, forward scattered light signal intensities that are observed in a discrete manner according to passage of the nanomaterial are approximately equivalent to intensities in the reference data. On the other hand, when the nanomaterial is in an aggregated state, because particle diameters are made large by the forming of aggregates, the forward scattered light signal intensities increase in comparison to the reference data. In aggregation state monitoring using side scattered light or backward scattered light from the nanomaterial, when the nanomaterial is in a well-dispersed state, side or backward scattered light signal intensities are approximately equivalent to those in the reference data. On the other hand, when the nanomaterial is in an aggregated state, due to formation of aggregates, the side or backward scattered light signal intensities decrease in comparison to the reference data.

In aggregation state monitoring using fluorescence from the nanomaterial, when the nanomaterial is in a well-dispersed state, fluorescence signal intensities that are observed in a discrete manner are approximately equivalent to those in the reference data. On the other hand, when the nanomaterial is in an aggregated state, the quantum effect of the nanomaterial disappears by the formation of aggregates, and the fluorescence signal intensities decrease or disappear in comparison to the reference data. By thus irradiating the passage region of the nanomaterial from the nozzle 20 to the substrate 10 with the monitoring light, and measuring the scattered light or the fluorescence generated from the nanomaterial, the dispersion state or aggregation state of the nanomaterial can be monitored optically and during execution of the sample preparation process.

In a case where the nanomaterial is judged to be in an aggregated state, by adjusting the value of the electrostatic spraying voltage applied to the dispersion liquid 13 by the voltage applying device 40, the sample preparation process can be executed while maintaining a well-dispersed state. For example, in a case where it is judged that the sprayed droplets are large due to the application voltage applied to the dispersion liquid 13 being too high and that aggregation of the nanomaterial is occurring consequently, the sample preparation process conditions can be adjusted by lowering the applied voltage within a range in which the electrostatic spraying itself is not stopped.

The observation sample preparation apparatus and observation sample preparation method according to the present invention are not restricted to the above-described embodiments and configuration examples, and various modifications are possible. For example, in regard to the configuration of the electrostatic spray nozzle, the configuration of the voltage application jig, etc., any of various specific configurations besides those of the above-described configuration examples may be employed. Also, for example, in regard to the application of the bias voltage to the grid portion of the substrate, the voltage may be applied by a configuration other than the voltage application jig.

Here, with the observation sample preparation apparatus according to the above-described embodiments, the configuration of the preparation apparatus that immobilizes the nanomaterial on the observation substrate and prepares the observation sample and includes: (1) the electrostatic spray nozzle, including the nozzle body, having a tubular structure capable of storing, in the interior thereof, the nanomaterial dispersion liquid, in which the nanomaterial is dispersed in the solvent, and having disposed, at the tip thereof, the dispersion liquid spray outlet for electrostatically spraying the nanomaterial dispersion liquid; (2) the substrate support, supporting the observation substrate, including the conductive grid portion, having the mesh-like form with one or a plurality of openings, and the nanomaterial supporting film, disposed at the opening of the grid portion and on which the nanomaterial to be observed is immobilized, so that the observation substrate opposes the dispersion liquid spray outlet of the electrostatic spray nozzle; (3) the reference electrode, disposed at the opposite side of the observation substrate from the electrostatic spray nozzle and so as to be spaced apart from the observation substrate and electrically connected to the reference potential; (4) the spraying voltage applying unit, applying the electrostatic spraying voltage between the nanomaterial dispersion liquid and the reference electrode; and (5) the adjustment voltage applying unit, applying the bias voltage, of the same polarity as the electrostatic spraying voltage and used for adjusting the position of immobilization of the nanomaterial on the observation substrate, between the grid portion of the observation substrate and the reference electrode; is employed.

With the observation sample preparation method according to the above-described embodiments, the configuration of the preparation method for immobilizing the nanomaterial onto the observation substrate and preparing the observation sample and including: (a) the dispersion liquid introducing step of using the electrostatic spray nozzle, including the nozzle body, having the tubular structure capable of storing, in the interior thereof, the nanomaterial dispersion liquid, in which the nanomaterial is dispersed in the solvent, and having disposed, at the tip thereof, the dispersion liquid spray outlet for electrostatically spraying the nanomaterial dispersion liquid, to introduce the nanomaterial dispersion liquid into the interior of the nozzle body; (b) the substrate setting step of setting the observation substrate, including the conductive grid portion, having the mesh-like form with one or a plurality of openings, and the nanomaterial supporting film, disposed at the opening of the grid portion and on which the nanomaterial to be observed is immobilized, so that the observation substrate opposes the dispersion liquid spray outlet of the electrostatic spray nozzle; (c) the spraying voltage applying step of applying, with respect to the reference electrode, disposed at the opposite side of the observation substrate from the electrostatic spray nozzle and so as to be spaced apart from the observation substrate and electrically connected to the reference potential, the electrostatic spraying voltage between the nanomaterial dispersion liquid and the reference electrode; (d) the adjustment voltage applying step of applying the bias voltage, of the same polarity as the electrostatic spraying voltage and used for adjusting the position of immobilization of the nanomaterial on the observation substrate, between the grid portion of the observation substrate and the reference electrode; and (e) the sample preparation step of immobilizing the nanomaterial on the observation substrate to prepare the observation sample by electrostatically spraying the nanomaterial dispersion liquid onto the observation substrate from the dispersion liquid spray outlet of the electrostatic spray nozzle and electrostatically depositing the nanomaterial on the surface of the observation substrate; is employed.

Preferably in the above-described configuration, the preparation apparatus includes the bias electrode, spaced apart from the reference electrode, electrically connected to the grid portion of the observation substrate, and applying the bias voltage from the adjustment voltage applying unit to the grid portion. Likewise, preferably in the preparation method, the bias voltage is applied to the grid portion via the bias electrode, spaced apart from the reference electrode and electrically connected to the grid portion of the observation substrate, in the adjustment voltage applying step. The bias voltage for immobilization position adjustment can thereby be applied favorably to the conductive grid portion.

In this case, the preparation apparatus may include the voltage application jig in which the reference electrode, the bias electrode, and the insulating layer disposed between the reference electrode and the bias electrode are integrated. Likewise, in the preparation method, the voltage application jig, in which the reference electrode, the bias electrode, and the insulating layer disposed between the reference electrode and the bias electrode are integrated, may be used in the adjustment voltage applying step. With these configurations, installation and connection with respect to the observation substrate and handling of the reference electrode and the bias electrode are facilitated.

Preferably in the above-described electrode configuration, the reference electrode is disposed so as to include the position opposing the nanomaterial supporting film of the observation substrate, and the bias electrode is disposed to enable the reference electrode to be in view from the nanomaterial supporting film. Adjustment of the nanomaterial immobilization position by application of the bias voltage can thereby be realized favorably.

In regard to the setting value of the bias voltage for immobilization position adjustment applied between the grid portion of the observation substrate and the reference electrode, the voltage is preferably set so that the absolute value (voltage magnitude) thereof is in the range of 5V to 50V. Electrostatic spraying of the nanomaterial dispersion liquid from the nozzle onto the substrate and adjustment of the nanomaterial trajectories and the immobilization positions on the substrate can thereby be combined favorably.

The preparation apparatus preferably includes the voltage controller controlling the electrostatic spraying voltage applied by the spraying voltage applying unit to achieve the condition where, in electrostatically spraying the nanomaterial dispersion liquid from the dispersion liquid spray outlet of the electrostatic spray nozzle onto the observation substrate, one or zero particles of the nanomaterial are contained in each individual droplet sprayed. Likewise, in the preparation method, electrostatic spraying of the nanomaterial dispersion liquid from the dispersion liquid spray outlet of the electrostatic spray nozzle onto the observation substrate is preferably performed under the condition where one or zero particles of the nanomaterial are contained in each individual droplet sprayed in the sample preparation step.

By thus performing electrostatic spraying of the dispersion liquid so that at most one particle of the nanomaterial is contained in each individual droplet sprayed, the nanomaterial in the droplet is prevented from forming an aggregate in the process of drying of the solvent. The nanomaterial can thereby be immobilized favorably in an adequately dispersed state on the nanomaterial supporting film of the observation substrate.

The present invention is applicable as an observation sample preparation apparatus and an observation sample preparation method with which an observation sample used for observation of a nanomaterial can be prepared in a satisfactory state.

From the invention thus described, it will be obvious that the invention may be varied in many ways. Such variations are not to be regarded as a departure from the spirit and scope of the invention, and all such modifications as would be obvious to one skilled in the art are intended for inclusion within the scope of the following claims.

What is claimed is:

1. An observation sample preparation apparatus, preparing an observation sample by immobilizing a nanomaterial on an observation substrate, the preparation apparatus comprising:
an electrostatic spray nozzle, comprising a nozzle body, having a tubular structure capable of storing, in an interior thereof, a nanomaterial dispersion liquid, in which a nanomaterial is dispersed in a solvent, and having a dispersion liquid spray outlet, provided at a tip of the tubular structure, for electrostatically spraying the nanomaterial dispersion liquid;
a substrate support, supporting an observation substrate, which includes a conductive grid portion having a mesh-like form with one or a plurality of openings and a nanomaterial supporting film disposed at the opening of the grid portion and on which the nanomaterial to be observed is immobilized, so that the observation substrate opposes the dispersion liquid spray outlet of the electrostatic spray nozzle;
a reference electrode, disposed at an opposite side of the observation substrate from the electrostatic spray nozzle and so as to be spaced apart from the observation substrate and electrically connected to a reference potential;
a spraying voltage applying unit, applying an electrostatic spraying voltage between the nanomaterial dispersion liquid and the reference electrode;
an adjustment voltage applying unit, applying a bias voltage, of the same polarity as the electrostatic spraying voltage and used for adjusting a position of immobilization of the nanomaterial on the observation substrate, between the grid portion of the observation substrate and the reference electrode; and
a bias electrode, spaced apart from the reference electrode, electrically connected to the grid portion of the observation substrate, and applying the bias voltage from the adjustment voltage applying unit to the grid portion.

2. The observation sample preparation apparatus according to claim 1, further comprising: a voltage application jig in which the reference electrode, the bias electrode, and an insulating layer disposed between the reference electrode and the bias electrode are integrated.

3. The observation sample preparation apparatus according to claim 1, wherein the reference electrode is disposed so as to include a position opposing the nanomaterial supporting film of the observation substrate, and
the bias electrode is disposed to enable the reference electrode to be in view from the nanomaterial supporting film.

4. The observation sample preparation apparatus according to claim 1, wherein the bias voltage is set so that an absolute value thereof is in the range of 5V to 50V.

5. The observation sample preparation apparatus according to claim 1, further comprising: a voltage controller, controlling the electrostatic spraying voltage applied by the spraying voltage applying unit to achieve a condition where, in electrostatically spraying the nanomaterial dispersion liquid from the dispersion liquid spray outlet of the electrostatic spray nozzle onto the observation substrate, one or zero particles of the nanomaterial are contained in each individual droplet sprayed.

* * * * *